United States Patent
Ohmura et al.

[11] Patent Number: 6,139,757
[45] Date of Patent: *Oct. 31, 2000

[54] METHOD OF SEPARATING CELLS FROM BLOOD USING A FILTER HAVING A CHANGEABLE POROSITY

[75] Inventors: Yoshitaka Ohmura; Noboru Taguchi; Tadashi Sameshima, all of Nakaimachi, Japan

[73] Assignee: Terumo Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/999,529

[22] Filed: Mar. 28, 1997

[30] Foreign Application Priority Data

| Mar. 28, 1996 | [JP] | Japan | 8-099199 |
| Sep. 13, 1996 | [JP] | Japan | 8-265313 |
| Feb. 26, 1997 | [JP] | Japan | 9-057115 |

[51] Int. Cl.⁷ .................................................. B01D 25/26
[52] U.S. Cl. ...................... 210/797; 210/489; 210/453; 210/351; 210/767; 435/2
[58] Field of Search ............... 435/2, 261; 210/650, 210/651, 767, 797, 453, 483, 488, 489, 350, 351

[56] References Cited

U.S. PATENT DOCUMENTS

| 3,747,769 | 7/1973 | Brumfield | 210/350 |
| 5,480,553 | 1/1996 | Yamamori et al. | 210/650 |
| 5,498,336 | 3/1996 | Katsurada et al. | 210/496 |
| 5,616,457 | 4/1997 | Garcia-Rubio . | |
| 5,643,772 | 7/1997 | Petersen et al. | 435/252.33 |
| 5,690,825 | 11/1997 | Parton | 210/350 |
| 5,695,989 | 12/1997 | Kalamasz | 435/308.1 |

*Primary Examiner*—Matthew O. Savage
*Assistant Examiner*—Terry K. Cecil
*Attorney, Agent, or Firm*—Burns, Doane, Swecker & Mathis, LLP

[57] ABSTRACT

A method of separating cells from blood by using a filter apparatus having first and second ports and a filter member therebetween having a changeable porosity. The filter member includes a stack of porous polymer sheets that preferably has a gradient of a physical or chemical characteristic in the direction of stacking. This can include a gradient in porosity, hydrophilicity or zeta potential. In a first step, blood is filtered through the apparatus when the filter member is set to a compressive state having a first porosity capable of capturing the objective cells. In a later step, the filter member is then set to a non-compressive state having a second porosity, higher than the first, for recovering the objective cells. The change in porosity results from the enlargement or reduction of the diameter of the pores of the filter member. The method can also include washing the filter member when the member is set to a porosity that is higher than the first porosity but lower than the second porosity.

15 Claims, 8 Drawing Sheets

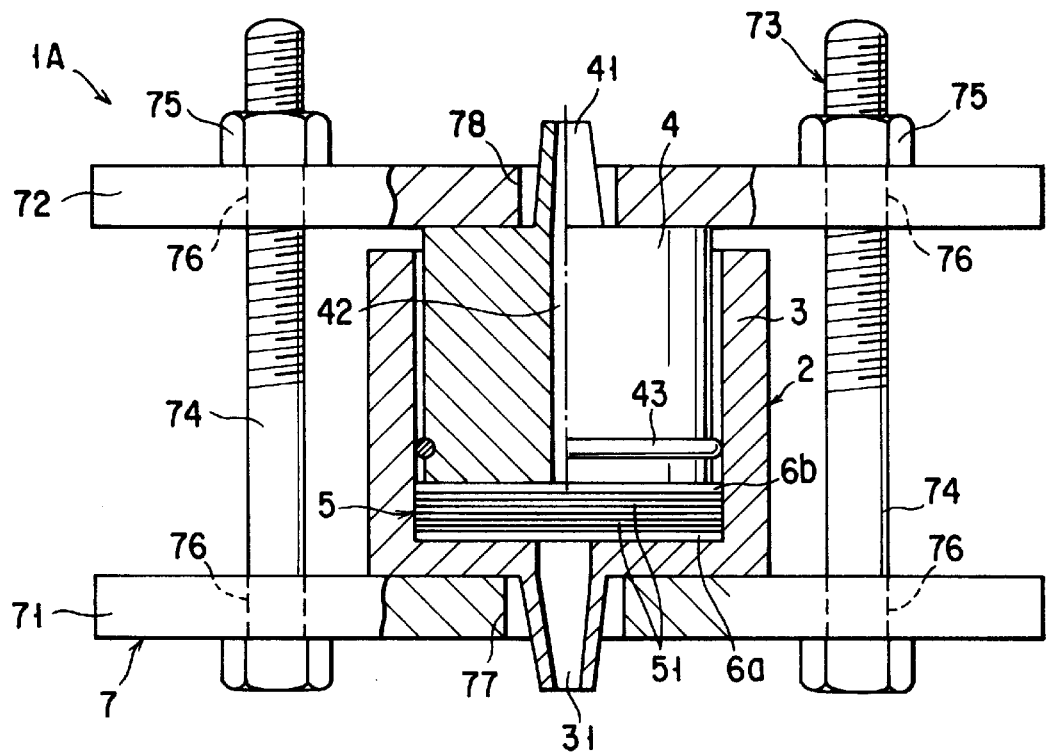
F I G. 2
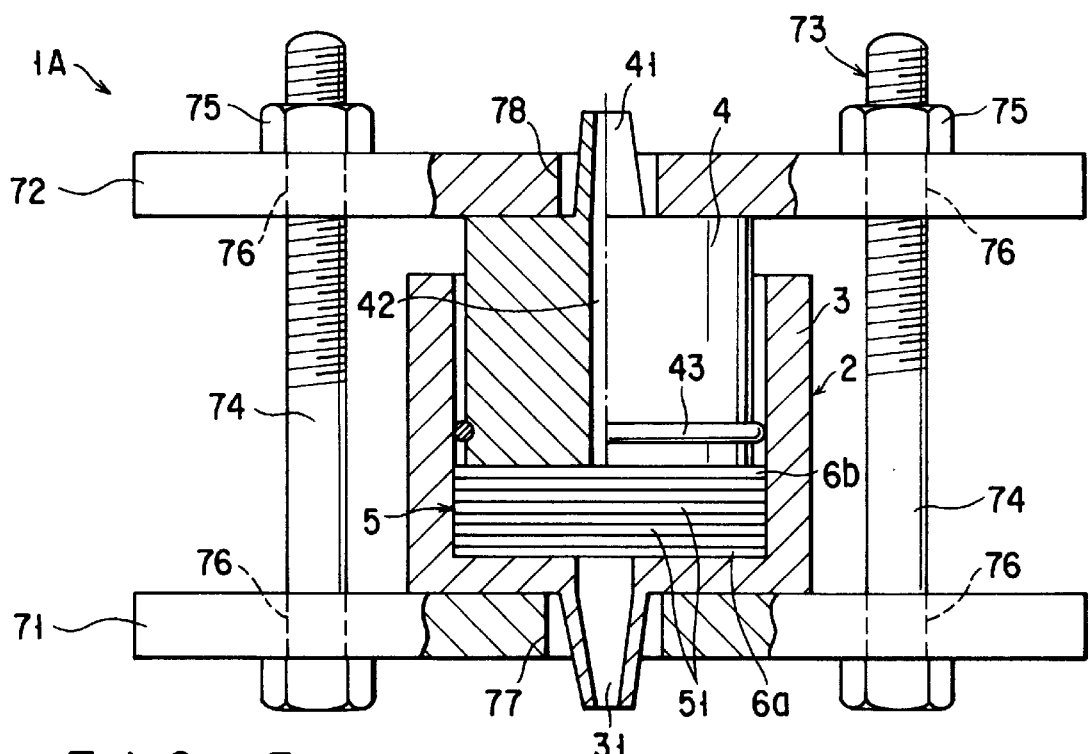
F I G. 3

METHOD OF SEPARATING CELLS FROM BLOOD USING A FILTER HAVING A CHANGEABLE POROSITY

BACKGROUND OF THE INVENTION

The present invention relates to a filter apparatus for separating objective micro-tissues of an organism such as cells from liquid which contain the micro-tissues, and to a method of separating micro-tissues of the organism using the same apparatus.

There has been performed separation or concentration of the objective cells such as lymphocyte (hereinafter called as "objective cells") from other components, when cells are handled outside of the organism, for example, in the case of culture and preservation of cells as well as in the case of therapy using cells, such as transplanting of bone marrow and hematopoietic stem cells, adoptive immuno-therapy, gene therapy and the like.

In the cell culture and the therapeutic treatment using cells, it has come out as an extremely significant subject to remove cells other than the objective cells, as well as unnecessary liquid components, wastes of cells and products produced by cells. In the case of using the preserved cells, it has also become a significant subject to remove the substance harmful to the cells and the living organism, such as the cryoprotective agent which is used in the cryopreservation. For this reason, there have been proposed various method for cell separation and suitable recovery methods corresponding to the cell separation.

Cell separation methods currently available are roughly classified as follows: (1) precipitation method, centrifugation method, and density-gradient centrifugation method, each using the difference of specific density of cells, (2) electrical separation method using the static charge on the cell-surface, (3) affinity separation method using the specificity of antibody to the antigen existing on the cell surface, and (4) filtration method using the difference in the size and the deformability of the cells, and the like.

However, the methods (1) to (4) respectively have the following problems.

In the precipitation method (1) using the difference in density of the cells, an excessively long time is required to separate the objective cells because the objective cells are separated by using gravity. Therefore, the separation efficiency is unsatisfactory and also the purity or yield is too low.

The centrifugal separation is a method capable of improving the separation efficiency of the precipitation method by using the centrifugal force, which has been used in general as a method of treating a large quantity of cells. However, the centrifugal separation method requires a large scale and expensive apparatus for aseptic treatment and recovery of cells. Moreover, in the centrifugal separation, the types of cells, which can be separated, are limited because the cells have only small differences in their density.

In order to improve the separation potential, there has been employed a density-gradient centrifugation method which uses specific density medium, wherein the specific density of the medium has been strictly adjusted. However, this method cannot simultaneously process a large quantity of cells. In addition, the objective cells must be carefully recovered from the interface which is formed due to the difference in the density. What is worse, the operation for removing unnecessary cell components and the operation for removing unnecessary liquid components must be performed under different conditions. Furthermore, a clean bench must be used to aseptically perform the recovery operation. As described above, the gradient-density centrifugation requires complicated operations.

Moreover, the method (1) may sometimes critically damages the objective cells if an unsuitable centrifugal condition is employed.

The electrical separation method (2) suffers from limited separation efficiency because of the small difference in the static charge on the cell-surface between different cells. Moreover, this method is unsuitable for quickly treating a large quantity of cells. What is worse, this method sometimes may cause damage of objective cells due to application of an electric field on the cells.

Although the affinity separation method (3) has the greatest specificity of the separation methods, an enzymatic process for cleavage of the adsorbed antibody molecules must be performed. Thus, technical problems arise because the enzymatic process damages the cells, the operation cannot easily be performed, and the activity of the antibody cannot easily be maintained. Moreover, the cost is excessively increased because of using expensive antibodies. Thus, this method is unsuitable to quickly treat a large quantity of cells.

The filtration method (4) is a method in which a cell suspension containing the objective cells are allowed to pass through a filter to capture the objective cells on the filter, and then recovery liquid is allowed to pass through the filter in a direction opposite to the foregoing step to detach the captured objective cells from the filter. This method is suitable to quickly separate objective cells in a large quantity from unnecessary cells and liquid components. However, this method has a problem of unsatisfactory efficiency in recovering objective cells. This problem is caused from the fact that the pore size of the filter is constant during the sequential processes for separation.

That is, if the pore size of the filter is enlarged to easily detach the captured objective cells, the quantity of the objective cells which are not captured and allowed to pass through the filter during the filtration is increased. If the pore size of the filter is made to be relatively smaller, the quantity of the objective cells allowed to pass through the filter can be reduced during the filtration and thus the quantity of the captured cells can be increased. However, adhesion properties of the objective cells with respect to the pores is enhanced. As a result, the detachment easiness of the captured cells from the filter is prevented. Thus, high recovery yield cannot be realized, and further, unnecessary cells cannot be removed satisfactorily.

In view of the foregoing problems, filters having appropriate pore size for attaining both requirements i.e., efficiency in capturing objective cells and satisfactory detachment easiness of captured cells, must be selected depending upon purpose of each use.

Incidentally, when the filtration method is performed such that the quantity of pressure of the cell suspension to be supplied for filtration is reduced, the quantity of the objective cells passing through the filter can be reduced to a certain extent and thus the capturing rate can be raised. In this case, however, the quantity which can be processed for unit time is reduced in the foregoing case. Therefore, the advantage of the filtration separation method capable of quickly treating a large quantity cannot be obtained.

On the other hand, when recovery of the objective cells are performed such that the quantity or pressure of the recovery liquid is increased, the detachment or easiness of the captured objective cells from the filter can be improved, resulting in high recovery of the objective cells. In this case, however, the objective cells are damaged considerably and, therefore, the characteristic and the quality of the recovered objective cells deteriorate.

As described above, the conventional methods have merits and demerits with respect to the means for separating the objective cells from unnecessary components and the means for recovering the separated cells. Thus, the conventional methods are used by being selected or combined with each other depending on the purpose and required levels of separation.

BRIEF SUMMARY OF THE INVENTION

The present invention aims to solve the problems experienced with conventional methods, in particular, the problems of the filtration separation method. An object of the present invention, therefore, is to provide a filter apparatus capable of easily and aseptically performing a required process suitable for a large scale separation, and enabling objective micro-tissues of the organism to be separated and recovered with a satisfactory yield without deterioration in the quality and the characteristic thereof.

The foregoing objects can be achieved by the following aspects (1) to (30) of the present invention.

(1) A filter apparatus comprising:
a housing having first and second ports; and
a filter member composed of a porous material, which is disposed in the housing, wherein
a porosity of the filter member can be set to be two or more different porosities.

(2) A filter apparatus comprising:
a housing having first and second ports; and
a filter member composed of a porous material, which is disposed in the housing so that inner space of the housing is partitioned into a first chamber communicated with the first port and a second chamber communicated with the second port; and
a means for changing porosity of the filter member, which can set the porosity of the filter member to a first porosity capable of capturing at least an objective micro-tissue to be separated and to a second porosity larger than the first porosity.

(3) A filter apparatus according to aspect (2), wherein the ratio of the second porosity with respect to the first porosity is 1.05 times to 3.0 times.

(4) A filter apparatus according to any one of aspects (1) to (3), wherein the filter member has a gradient of physical or a chemical characteristic in a direction along which fluid flows.

(5) A filter apparatus according to any one of aspects (1) to (4), wherein the filter member comprises a plurality of porous materials, and all or a part of the plural porous materials has a gradient of physical or chemical characteristic.

(6) A filter apparatus according to aspect (4) or (5), wherein the gradient of physical or chemical characteristic comprises change of the pore size of the porous material.

(7) A filter apparatus according to aspect (4) or (5), wherein the gradient of physical or chemical characteristic comprises change of the porosity of the porous material.

(8) A filter apparatus according to aspect (4) or (5), wherein the gradient of physical or chemical characteristic comprises the hydrophilicity of the porous material.

(9) A filter apparatus according to aspect (4) or (5), wherein the gradient of physical or chemical characteristic comprises change of the zeta potential of the porous material.

(10) A filter apparatus according to any one of aspects (1) to (9), wherein the filter member is elastically deformable, and the porosity thereof is adjusted by compressing the filter member to lower the porosity or by releasing or weakening the compressive force to raise the porosity.

(11) A filter apparatus according to any one of aspects (1) to (9), wherein the filter member is elastically deformable, and the porosity thereof is adjusted by stretching the filter member to raise the porosity or by releasing or weakening the stretching force to lower the porosity.

(12) A filter apparatus according to any one of aspects (1) to (11), wherein the filter member has such a structure such that rise and lowering of the porosity correspond to enlargement and reduction of the diameter of the pores, respectively.

(13) A filter apparatus according to any one of aspects (1) to (12), wherein the change of the porosity of the filter member is caused with accompanied by volumetric change of the housing.

(14) A filter apparatus according to any one of aspects (1) to (13), wherein the housing comprises a first housing member and a second housing member capable of moving in a liquid-tight fashion with respect to the first housing member, and relative movement of the second housing member with respect to the first housing member causes deformation of the filter member so as to change the porosity of the filter member.

(15) A filter apparatus according to aspect (14), further comprising at least one seal member for maintaining the liquid-tightness between the first housing member and the second housing member.

(16) A filter apparatus according to any one of aspects (1) to (15), further comprising a fluid-passage maintaining member for maintaining a flowing passage of liquid which is introduced through the first port and/or the second port to the filter member.

(17) A method of separating objective micro-tissues of an organism by using a filter member made of a porous material having a porosity which can be changed, the method comprising the steps of:
filtering the micro-tissues of an organism body by using the filter member which is in such a state that the porosity of the filter member has been set to a first porosity capable of capturing the objective micro-tissues; and
recovering the objective micro-tissues captured by the filter member, the recovery being performed in such a state that the porosity of the filter member has been set to a second porosity which is higher than the first porosity.

(18) A method of separating objective micro-tissues of an organism by using a filter apparatus which comprises a housing having first and second ports and accommodates a filter member made of porous material having a variable porosity, the method comprising the steps of:
supplying liquid to be treated containing the micro-tissues of an organism through the first port to the filter member and separate the objective micro-tissues by passing the liquid through the filter member in such a state that the porosity of the filter member has been set to a first porosity capable of capturing the objective micro-tissues; and
supplying recovering liquid through the second port to the filter member in such a state that the porosity of the filter member has been set to a second porosity which is higher than the first porosity, thereby recovering the objective micro-tissues captured by the filter member.

(19) A method of separating objective micro-tissues of an organism by using a filter apparatus which comprises a housing having first and second ports and accommodates a filter member made of porous material having a variable porosity, the method comprising the steps of:

supplying liquid to be treated containing the micro-tissues of an organism through the first port to the filter member and separate the objective micro-tissues by passing the liquid through the filter member in such a state that the porosity of the filter member has been set to a first porosity capable of capturing the objective micro-tissues;

supplying washing liquid through the first port, thereby washing the filter member; and supplying recovering liquid through the second port to the filter member in such a state that the porosity of the filter member has been set to a second porosity which is higher than the first porosity, thereby recovering the objective micro-tissues captured by the filter member.

(20) A method of separating objective micro-tissues of an organism according to aspect (19), wherein the washing step of the filter member is performed in such a state that the porosity of the filter member has been set to a level which is higher than the first porosity and lower than the second porosity.

(21) A method of separating objective micro-tissues of an organism according to aspect (19), wherein the washing step of the filter member is performed in such a state that the first porosity of the filter member is retained.

(22) A method of separating objective micro-tissues of an organism according to any one of aspects (17) to (21), wherein the ratio of the second porosity with respect to the first porosity is 1.05 times to 3.0 times.

(23) A method of separating objective micro-tissues of an organism according to any one of aspects (17) to (22), wherein the filter member comprises a laminate of a plurality of porous film.

(24) A method of separating objective micro-tissues of an organism according to any one of aspects (17) to (23), wherein the filter member has a gradient of physical or a chemical characteristic in a direction along which the liquid flows.

(25) A method of separating objective micro-tissues of an organism according to aspect (24), wherein the gradient of physical or chemical characteristic comprises change of the pore size of the porous material.

(26) A method of separating objective micro-tissues of an organism according to aspect (24), wherein the gradient of physical or chemical characteristic comprises change of the porosity of the porous material.

(27) A method of separating objective micro-tissues of an organism according to aspect (24), wherein the gradient of physical or chemical characteristic comprises change of the hydrophilicity of the porous material.

(28) A method of separating objective micro-tissues of an organism according to aspect (24), wherein the gradient of physical or chemical characteristic comprises change of the zeta potential of the porous material.

(29) A method of separating objective micro-tissues of an organism according to any one of aspects (17) to (28), wherein the filter member has such a structure that rise and lowering of the porosity correspond to enlargement and reduction of the pore size, respectively.

(30) A method of separating objective micro-tissues of an organism according to any one of aspects (18) to (21), further comprising a fluid-passage maintaining member for maintaining a flowing passage of liquid which is introduced through the first port and/or the second port to the filter member.

Additional objects advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a cross sectional side view showing a working state of the filter apparatus according to the first embodiment;

FIG. 3 is a cross sectional side view showing a working state of the filter apparatus according to the first embodiment;

DETAILED DESCRIPTION OF THE INVENTION

Figure 1:
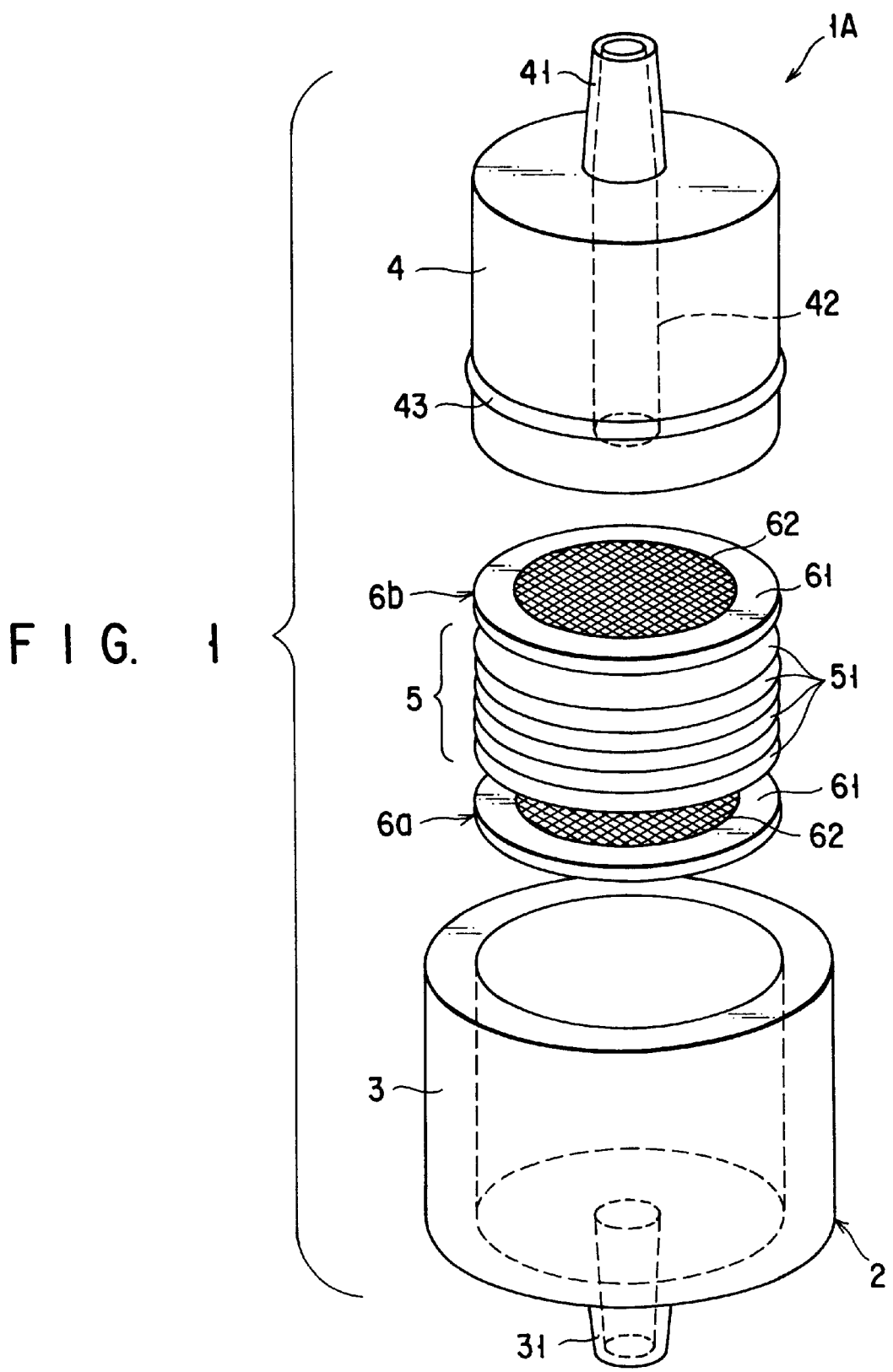
FIG. 1 is an exploded perspective view showing a first embodiment of a filter apparatus according to the present invention.

The present invention is applied for separating, or for separating, washing and recovering objective micro-tissues (hereinafter representatively referred as "cells") of an organism from liquid, i.e. liquid to be processed containing body fluids, such as blood, blood components, lymph, urine and bile, as well as preservation, culture medium, washing solution, cryoprotectant and other components (cells etc.) other than the objective cells.

In the present invention, a filter member for filtering or capturing objective cells is made of a porous material, particularly, a porous polymer material. More preferably, use is made of a porous polymer member having a characteristic which is physically or chemically changed in the direction along which the liquid flows, i.e., the filtration direction. It is preferable to employ a filter member which can be elastically deformed, that is, a filter member having restoring force from compressed or stretched sate. A first embodiment of such filter member is that which has, in a usual state, a predetermined second porosity (a second pore size) and has, in a compressed state, a first porosity (a first pore size) lower than the second porosity or the second pore size. If the filter member is that which can be elastically deformed, it is restored to the original state having the porosity substantially equal to the second porosity (the second pore size) after the compressive force has been released.

A second embodiment of the filter member described above is that which has, in usual state, a predetermined first porosity (the first pore size) and has, in an stretched state, a second porosity (the second pore size) higher than the first porosity or the second pore size. If the filter member is that which can elastically be deformed, it is restored to the original state having the porosity substantially equal to the first porosity (the first pore size) after the stretching force has been canceled. According to the present invention, external force for compressing or stretching the filter member is applied onto the filter member, thereby changing porosity thereof during the sequential process from filtration (capture) to the recovery of the objective cells.

That is, when the objective cells are filtered, the porosity of the filter member is set to the first porosity (the first pore size) having a low level in order to capture a sufficiently large quantity of the objective cells. When the captured objective cells are recovered, the porosity of the filter member is set to be the second porosity (the second pore size) having a high level in order to enhance the detachment of the objective cells to reduce the quantity of the remaining objective cells in the filter member so as to improve the recovery ratio. In the case that employs a filter member having a gradient of chemical or physical characteristics in the direction along which the liquid flows, the separation and the recovery are carried out as follows. When the objective cells are filtered, the porosity of the filter member is set to the first porosity (the first pore size) of the low level, and the physical or chemical characteristics of the filter member are effectively utilized, thereby capturing a sufficiently large quantity of the objective cells. When the captured objective cells are recovered, the porosity of the filter member is set to the second porosity (the second pore size) of high level and the physical or chemical characteristics of the filter member are effectively used to enhance the detachment of the captured objective cells, so as to reduce the quantity of the objective cells remaining in the filter member, thereby improving the recovery ratio.

In the foregoing cases, it is preferable that the direction along which the liquid flows during the filtration step is opposite to the liquid-flow direction during the recovering step, with respect to the filter member. The inner portion of the housing, particularly, the filter member, may be washed to remove unnecessary components prior to recovering the objective cells. As a result of the washing step, the removal ratio of the unnecessary components in the recovered objective cells can be improved. The present invention having the above-mentioned features enables a quick and large quantity process to be performed by a simple operation without damage and activation of the cells. As a result, not only the yield of the objective cells can be significantly improved, but also the removal ratio of unnecessary components can be enhanced.

The filter apparatus and a method of separating microtissues of the organism according to the present invention will now be described in detail by referring to the preferred embodiments shown in the attached drawings.

Figure 4:
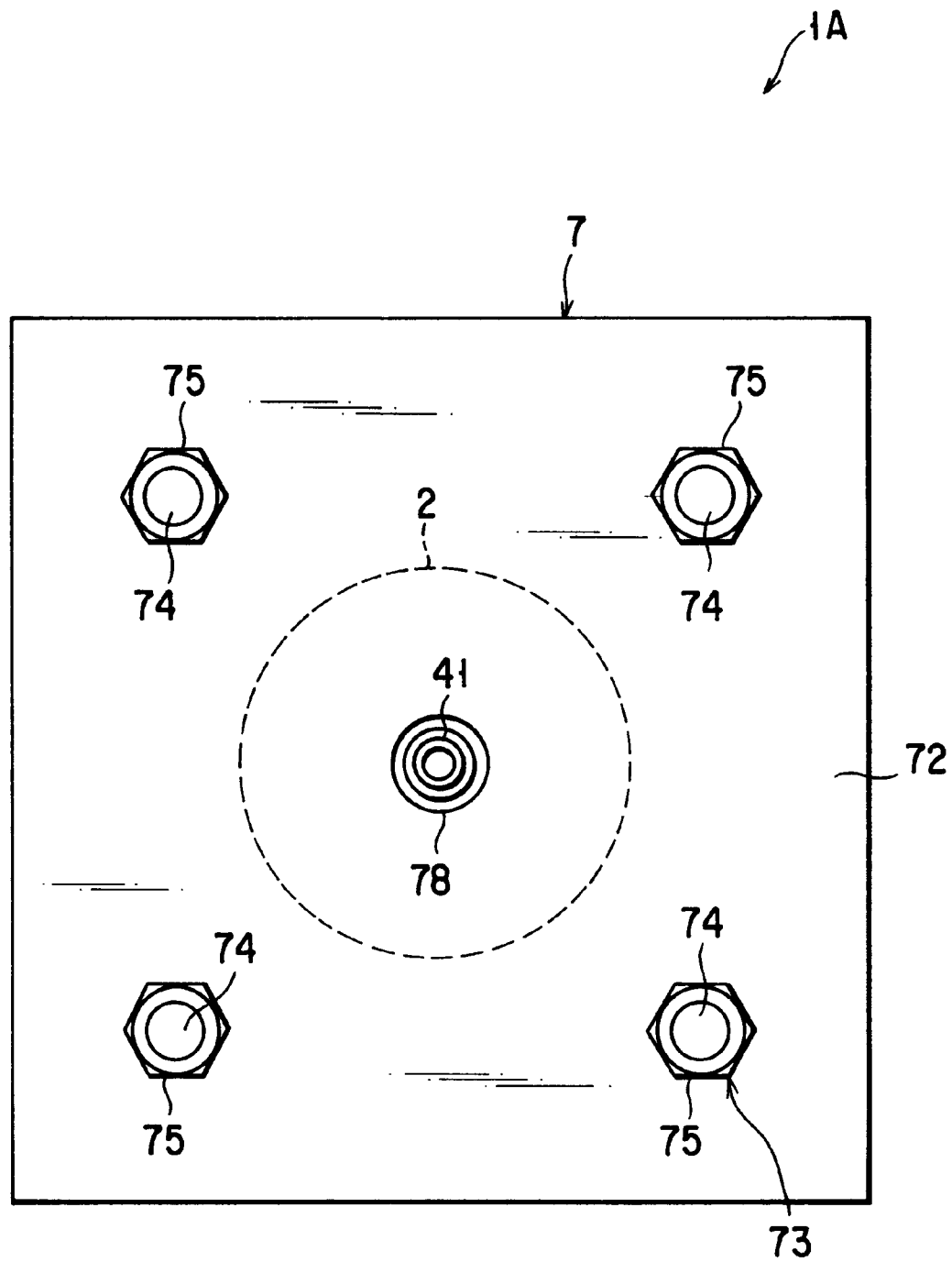
FIG. 4 is a plan view showing the filter apparatus shown in FIG. 2.

FIG. 1 is an exploded perspective view showing a first embodiment of the filter apparatus according to the present invention. FIGS. 2 and 3 are cross sectional side views each showing a working state of the filter apparatus according to the first embodiment. FIG. 4 is a plan view showing the filter apparatus shown in FIG. 2

As shown in FIGS. 1 to 3, a filter apparatus 1A according to the present invention is mainly composed of a housing 2, a filter member 5 which is disposed in the housing 2 and made of a porous material, flow-passage maintaining members 6a and 6b and a porosity changing means for setting the porosity of the filter member 5.

The housing 2 comprises a first housing member 3 in the form of a cylinder having bottoms; and a second housing member 4 arranged to be inserted into the first housing member 3 and having a substantially cylindrical shape.

The first housing member 3 has, in the bottom portion thereof, a first port (an inlet port for liquid to be processed) 31 which communicates with the inside portion of the housing 2, the first port being projected downward from the bottom portion.

In the central portion of the second housing member 4, a lumen 42 which penetrates through the second housing member 4 is formed along the axial direction thereof. The second housing member 4 has, at the top end thereof, a second port (an outlet port of the filtrate) 41 which communicates with the lumen 42.

A seal ring (a seal member) 43, made of an elastic material such as rubber or a thermoplastic elastomer, is disposed in the outer periphery of the second housing member 4. When the second housing member 4 has been inserted into the first housing member 3, the seal ring 43 is brought into close contact with the inner surface of the first housing member 3 in order to maintain the liquid-tightness of the housing 2, particularly, the aseptic characteristic.

When the second housing member 4 is moved with respect to the first housing member 3 in the axial direction, the seal ring 43 slides while being in close contact with the inner surface of the first housing member 3.

The filter member 5 is formed by stacking a plurality of porous polymer sheets 51. It is preferable that each of the porous polymer sheets 51 made of a material which is hard to be plastically deformed even if external force, such as compressive or stretching force, is applied and which is restorable upon removal of the external force. Specifically, the porous polymer sheets 51 includes, for example, those which have been made of polyurethane, styrene-butadiene rubber, polyvinyl alcohol, polypropylene, polyether polyamide and other polymer materials.

Since each of the porous polymer sheets 51 of the filter member 5 according to this embodiment is, as shown in FIG. 2, consolidated when a predetermined compressive force (external force) is applied to the filter member 5, the porosity of each of the porous polymer sheets 51 is made to be the first porosity which is lower than a second porosity to be described later. The first porosity is set to be suitable to capture (filter and separate) the objective cells.

As shown in FIG. 3, in a state where no compressive force (external force) is applied (that is, in a state where the compressive force has been released) or in a state where the compressive force has been loosen, the porosity is set to be the second porosity which is suitable to detach and recover the captured objective cells.

The ratio of the second porosity with respect to the first porosity may be arbitrarily depending upon various conditions including the type and size of the objective cells. It is preferable, however, that the ratio is usually about 1.05 times to about 3 times, more preferably about 1.10 times to about 2.0 times. If the ratio is lower than 1.05, the required effect to improve the yield of the objective cells by changing the porosity cannot sometimes be obtained depending upon the conditions, such as the type and size of the objective cells. If the ratio is higher than 3, the first porosity is become to be lower than 33% and thus the passing easiness of the liquid to be processed including the objective cells excessively deteriorates.

Supposed that the average pore size of the filter member 5 in the compressed state is the first pore size and the average pore size in a state where the compressive force applied to the filter member 5 has been removed is the second pore size, the first and second pore size are also arbitrarily determined depending upon various conditions including the type and size of the objective cells. If the objective cells are lymphocyte, however, it is preferable that the first pore size is smaller than 5 $\mu$m, more preferably 2 $\mu$m to 4.9 $\mu$m. On the other hand, it is preferable that the second pore size is 5 $\mu$m or greater, more preferably 6 $\mu$m or greater.

Although the filter member 5 may have a structure such that the porous polymer sheets 51 are made of the same material, it is preferable that the porous polymer sheets 51 have a gradient (change) of the physical or chemical characteristics. More particularly, it is preferable that all or some of the porous polymer sheets 51 have different physical or chemical characteristics. The difference in the physical or chemical characteristics enables the objective cells to easily be captured during the filtering step, as well as to easily be detached from the filter member during the recovering step.

The physical or chemical characteristics that may be set as a gradient fashion is selected by considering, as one factor for determining the filtering condition, the various characteristics including the type, size, and the like of the objective cells so that the gradient of the selected characteristic improve at least one of easiness for capturing the objective cells by the filter member and easiness for detaching the captured cells from the filter member.

The gradient is realized by, for example, a structure in which the porous polymer sheets are stacked in such a manner that at least any one of the average pore size, the zeta potential or the hydrophilicity is changed continuously or stepwise in the direction along which the liquid allowed to flow.

A stacked structure for changing the average pore size can be realized by a method in which the porous polymer sheets 51 are sequentially stacked in such a manner that the average pore diameter is reduced in a direction from the first port 31 to the second port 41.

A stacked structure for changing the zeta potential can be realized by a method in which the porous polymer sheets 51 are sequentially stacked in such a manner that the zeta potential is enhanced in a direction from the first port 31 to the second port 41, particularly, the zeta potential is changed from negative level to the positive level.

A stacked structure for changing the hydrophilicity can be realized by a method in which the porous polymer sheets 51 are sequentially stacked in such a manner that the hydrophilicity increases from the first port 31 to the second port 41.

The orientation of the gradient is not limited to the foregoing description, and may arbitrarily be changed depending upon types of the objective cells.

The flow-passage maintaining members 6a and 6b respectively are stacked and mounted on the top and bottom surface of the filter member 5, and accommodated in the housing 2 together with the mounted members 6a and 6b. Each of the flow-passage maintaining members 6a and 6b is composed of a ring 61 made of a flexible material, such as silicone, and a mesh (a diffusion member) 62 inserted into the inside portion of the ring 61. The ring 61 has a thickness of, for example, about 1 mm to about 10 mm.

When the flow-passage maintaining member 6a is disposed, a space communicated with the first port 31 is formed in the ring 61. Thus, a flow passage for the solution introduced through the first port 31 to the filter member 5 is maintained. When the flow-passage maintaining member 6b is disposed, a space communicated with the second port 41 is formed in the ring 61. Thus, a flow passage for the solution introduced through the first port 41 to the filter member 5 is maintained. As a result, the filter member 5 is disposed in the housing 2 so that the space communicated with the first port 31 and the space communicated with the second port 41 are separated from each other.

Since flow-passage maintaining members 6a and 6b are structured such that the mesh 62 is disposed in the ring 61, liquid, which flows through the internal space of the ring 61, is uniformly dispersed (diffused) in the direction of the surface of the filter member 5. As a result, efficiencies of the filtration, washing and objective cell recovery can be improved.

As shown in FIGS. 2 to 4, the porosity changing means 7 comprises a pair of plate members 71 and 72 and a distance setting means 73 for setting the distance between the plate members 71 and 72. The distance setting means 73 according to this embodiment is composed of four sets of bolts 74 and nuts 75.

Each of the plate members 71 and 72 has an insertion holes 76 for receiving each bolt 74. An opening 77, through which the first port 31 is allowed to pass, is formed in substantially the central portion of the plate member 71, while an opening 78, through which the second port 41 is allowed to pass, is formed in substantially the central portion of the plate member 72.

The housing 2 accommodating the filter member 5 and the flow-passage maintaining members 6a and 6b are inserted between the plate members 71 and 72, followed by inserting the four bolts 74 into the plate members 71 and 72. Then, the nuts 75 for the bolts 74 are set. By changing the angular degree of rotation of each nuts 75 with respect to each bolts 74, the distance between the plate members 71 and 72 is adjusted and determined.

Since the housing 2 is brought to a state in which the bottom surface of the first housing member 3 is in contact with the plate member 71 and the top surface of the second housing member 4 is in contact with the plate member 72, the insertion depth of the second housing member 4 with respect to the first housing member 3 can be adjusted in accordance with the distance between the plate members 71 and 72. The insertion depth corresponds to the compressive force acting on the filter member 5. Therefore, the porosity (the pore size) of the filter member 5 can be adjusted by the compressive force.

The insertion depth of the second housing member 4 with respect to the first housing member 3 corresponds to the volumetric capacity of the housing 2. Therefore, the porosity (the pore size) of the filter member 5 is increased or decreased together with enlargement or reduction of the capacity of the housing 2. As a result, a dead space in the housing 2 can be reduced so that a required flow passage to the filter member 5 is maintained. Thus, the priming quantity can be reduced and the yield of the objective cells can be improved.

An embodiment of the method of separating micro-tissues of an organism using the filter apparatus 1A, which is in accordance with the present invention will now be described.

1-A

As shown in FIG. 2, the porosity changing means 7 is initially operated as described above so as to hold the housing 2, and further, the insertion depth of the second housing member 4 with respect to the first housing member 3, that is, the compressive force acting on the filter member 5 is adjusted to a required level. Then, the pore size of the filter member 5 is set to be the first pore size capable of capturing the objective cells.

2-A

Then, cell suspension solution (liquid to be processed) including the objective cells, for example, blood, the blood component (for example, buffy coat) or bone marrow, is supplied into the housing 2. When the cell suspension solution flows in the ring 61 of the flow-passage maintaining member 6a, the flow of the cell suspension solution is uniformly dispersed in a radial direction from the central portion of the filter member 5 so as to be caused to pass through each of the porous polymer sheets 51. At this time, the objective cells cannot pass through the pores of the porous polymer sheets 51 set to be the first pore size and thus captured. Other components (the unnecessary components) are allowed to pass through the pores, and then to sequentially pass through the flow-passage maintaining member 6b and the inner cavity 42 of the second housing member 4, and thereafter, the other components are discharged through the second port 41. As described above, the objective cells can be separated from the cell suspension solution.

3-A

When filtration of the objective cells have been completed, washing solution is supplied through the first port 31 to wash the inside of the housing 2, particularly, the filter member 5. As a result, the unnecessary components adhere to the inner surface of the housing 2 and the filter member 5 can be washed off so as to be discharged through the second port 41. As a result of the foregoing washing operation, the removal ratio of the unnecessary components in the recovered objective cells can be enhanced.

As the washing solution, for example, buffer such as phosphate buffer, citrate buffer and borate buffer, culture medium, cryoprotectant, serum, plasma and physiological salt solution are exemplified.

It is preferable that the washing step be performed in a state where the porosity changing means 7 sets the porosity (the pore size) of the filter member 5 to be no lower than the first porosity (the first pore size) and no higher than the second porosity (the second pore size). More particularly, it is preferable that the process be performed in a state where the porosity of the filter member 5 is retained to be the first porosity (the first pore size). As a result, it can be prevented that the objective cells captured by the filter member 5 are unintentionally removed together with the unnecessary components. Thus, lowering of the recovery ratio of the objective cells can be prevented.

The foregoing washing process may arbitrarily be performed and it may be omitted.

4-A

Then, the porosity changing means 7 is, as shown in FIG. 3, operated to release the housing 2 or to weaken the holding force. Then, the second housing member 4 slides in a direction in which the second housing member 4 is moved away from the first housing member 3, if necessary. Thus, the capacity of the housing 2 is enlarged. As a result, the compressive force acting on the filter member 5 is released or weakened so that the filter member 5 is expanded due to the own restoring force so that the pore size of the filter member 5 is set to be the second pore size.

5-A

In the foregoing state, liquid for recovering objective cells is supplied through the second port 41. The supplied liquid is allowed to pass through the inner cavity 42. When the recovering liquid passes through the ring 61 of the flow-passage maintaining member 6b, the flow of the solution is uniformly dispersed in a radial direction from the central portion of the filter member 5 so as to be allowed to pass through the porous polymer sheets 51 of the filter member 5. At this time, the objective cells captured by the filter member 5 are enabled to easily pass through the pores because the pore size has been enlarged to the second pore size. As a result, the objective cells are, with the flow of the recovering liquid, allowed to pass through the flow-passage maintaining member 6a so as to be discharged through the first port 31 and recovered.

The liquid for recovering the objective cells, liquid similar to the washing liquid may be employed.

As a result of the method of separating cells designed as described above, the recovery ratio of the objective cells and the removal ratio of matters except the objective cells can significantly be improved.

Figure 5:
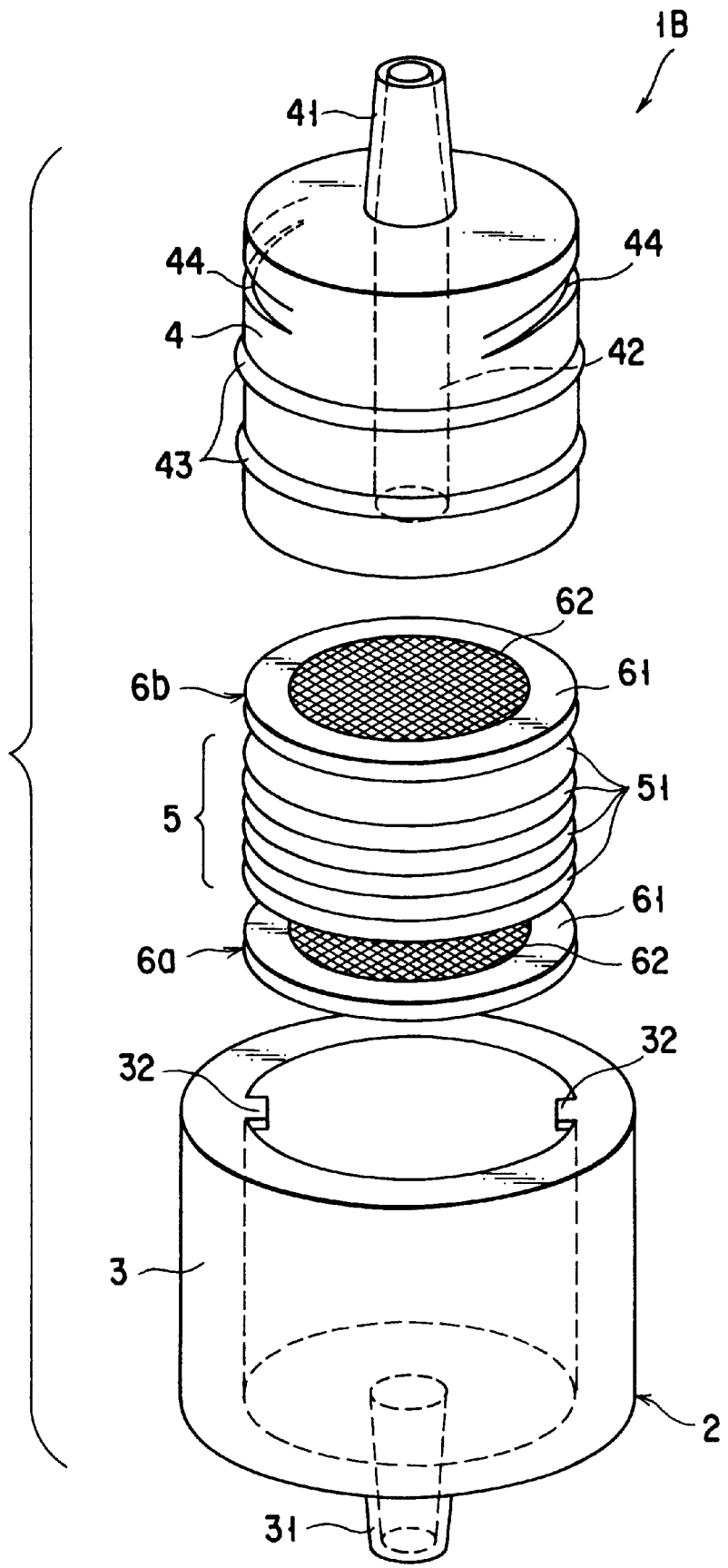
FIG. 5 is an exploded perspective view showing a second embodiment of the filter apparatus according to the present invention.
Figure 6:
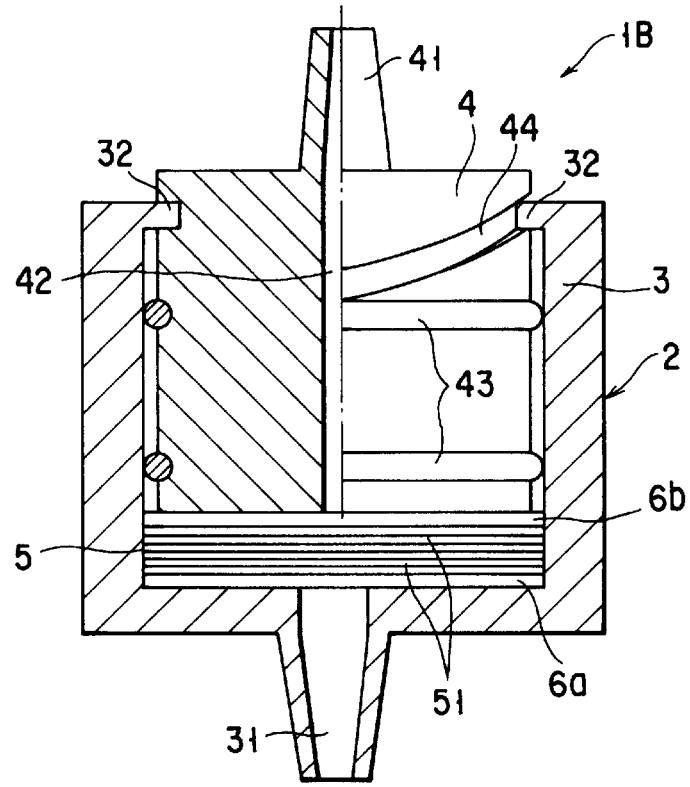
FIG. 6 is a cross sectional side view showing a working state of the filter apparatus according to the second embodiment.
Figure 7:
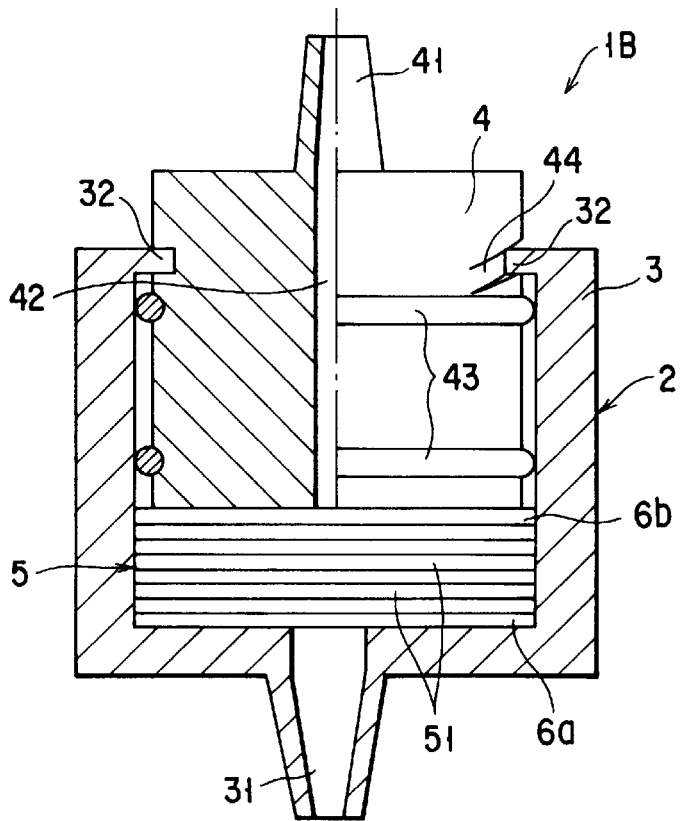
FIG. 7 is a cross sectional side view showing a working state of the filter apparatus according to the second embodiment.

FIG. 5 is an exploded perspective view showing a second embodiment of the filter apparatus according to the present invention. FIGS. 6 and 7 are cross sectional side views showing a working state where the filter apparatus according to the second embodiment is used. The filter apparatus 1B shown in FIGS. 5 to 7 will now be described such that the difference from the filter apparatus 1A is mainly described and similar elements are omitted from description.

The filter apparatus 1B has a housing 2, a filter member 5 disposed in the housing 2 and having a structure similar to the foregoing embodiment, and flow-passage maintaining members 6a and 6b.

The second housing member 4 has, in the periphery thereof, two seal rings (seal members) 43 each having a structure similar to the foregoing embodiment, are disposed apart from each other for a predetermined distance in the axial direction. When the second housing member 4 has been inserted into the first housing member 3, the two seal rings 43 are brought into close contact with the inner surface of the first housing member 3 so that liquid-tightness of the housing 2, particularly, the aseptic characteristic thereof is maintained.

When the second housing member 4 is, in the axial direction, moved with respect to the first housing member 3, the seal ring 43 slides while being brought into close contact with the inner surface of the first housing member 3. Since the two seal rings 43 are disposed apart from each other, the aseptic characteristic of the processing space in which the filter member 5 has been accommodated can be maintained during the axial direction movement of the second housing member 4.

The filter member 5 and the flow-passage maintaining members 6a and 6b of the filter apparatus 1B are structured similarly to the previously-mentioned embodiment.

The filter apparatus 1B has porosity changing means for changing the porosity of the filter member 5. The porosity changing means is composed of: a pair of projections 32 working as thread which are formed in the upper portion of the first housing member 3 as to project inwards; and a pair (two) of spiral thread grooves 44 formed on the outer surface of the second housing member 4, which correspond and engage to the thread projections 32. Each of the thread projections 32 is inserted and engaged to the corresponding thread groove 44.

When the second housing member 4 is rotated relative to the first housing member 3, each of the thread projections 32 slides along the corresponding thread groove 44 so that the second housing member 4 is moved with respect to the first housing member 3 in the axial direction.

The shape and number of the thread projection 32 are not limited to the illustrated structure. For example, a continuous thread projection may be employed. Also the shape and pattern of the thread grooves 44 are not limited.

When the second housing member 4 is rotated in, for example, a leftward direction with respect to the first housing member 3 in a state where the filter member 5 and the flow-passage maintaining members 6a and 6b are accommodated in the housing 2 (i.e., the filter apparatus 1B has been assembled), the second housing member 4 is moved such that the second housing member 4 is inserted deeply in the first housing member 3. On the contrary, when the second housing member 4 is rotated in the rightward direction with respect to the first housing member 3, the second housing member 4 is moved in a direction in which the second housing member 4 is separated from the first housing member 3. As described above, the relative amount of rotation of the second housing member 4 with respect to the first housing member 3, that is, the degree of screw engagement of the screw thread projections 32 with respect to the thread grooves 44, is adjusted and determined so that the insertion depth of the second housing member 4 with respect to the first housing member 3 is adjusted. The insertion depth corresponds to the compressive force acting on the filter member 5. Thus, the porosity (the pore size) of the filter member 5 can be adjusted.

The insertion depth of the second housing member 4 with respect to the first housing member 3 corresponds to the volumetric capacity of the housing 2. Therefore, the porosity (the pore size) of the filter member 5 is raised or lowered together with enlargement or reduction of the capacity of the housing 2. As a result, a dead space in the housing 2 can be reduced in such a manner that a required flow passage to the filter member 5 is maintained. Thus, the priming quantity can be reduced and the yield of the objective cells can be improved.

The method of separating micro-tissues of an organism using the filter apparatus 1B, which is in accordance with the present invention, is similar to that adapted to the filter apparatus 1A except that the operation of the porosity changing means in the forgoing steps [1-A] and [4-A] being performed by adjusting the rotational direction of the second housing member 4 with respect to the first housing member 3 and the amount of the rotation.

In the cell separation method in the second embodiment also, the recovery ratio of the objective cells and the removal ratio of matters except the objective cells are significantly improved.

Figure 8:
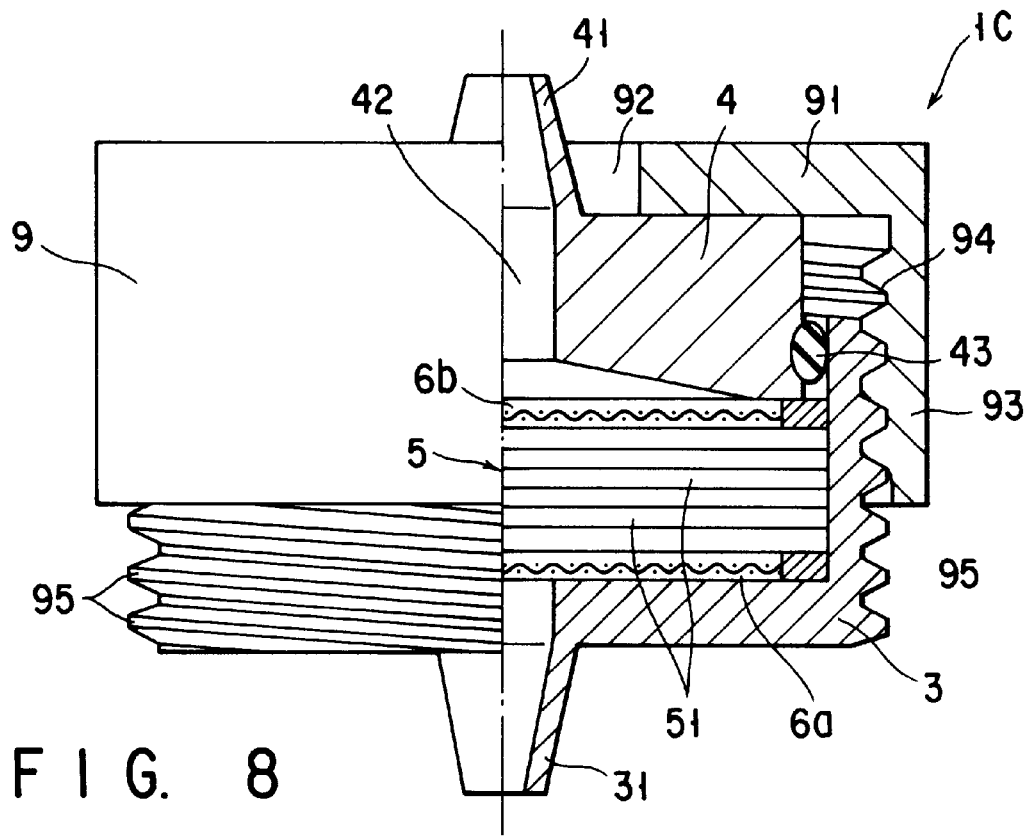
FIG. 8 is a partial cross sectional side view showing a third embodiment of the filter apparatus according to the present invention.
Figure 9:
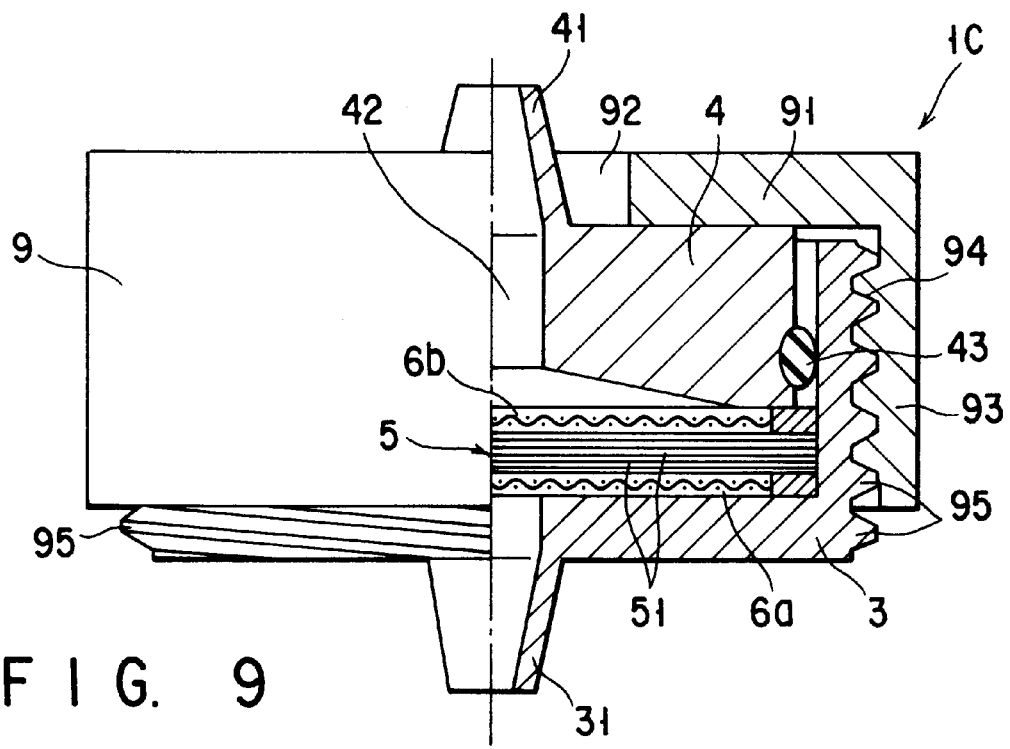
FIG. 9 is a partial cross sectional side view showing the third embodiment of the filter apparatus according to the present invention.

FIGS. 8 and 9 are partial and cross sectional side views showing a third embodiment of the filter apparatus according to the present invention. Elements of a filter apparatus 1C shown in FIGS. 8 and 9 which are different from those of the filter apparatus 1A will mainly be described and similar elements are omitted from description.

The filter apparatus 1C has a housing 2, a filter member 5 which is disposed in the housing 2 and has a structure similar to the previously described embodiment, and flow-passage maintaining members 6a and 6b.

The housing 2 comprises a first housing member 3 in the form of a cylinder having bottoms, and a second housing member 4 inserted into the first housing member 3.

A first port 31 (an inlet port for liquid to be processed) communicated with the inside portion of the housing 2 is formed in the bottom portion of the first housing member 3, which projects downward from the surface of the bottom portion. Moreover, a male thread 95 is formed in the outer periphery of the first housing member 3.

The second housing member 4 has, in the central portion thereof, a lumen 42 penetrating the second housing member 4 in the axial direction of the second housing member 4. The second housing member 4 has, at the top end thereof, a second port (an outlet for the filtrate) 41 communicated with the lumen 42, which projects upward from the top surface of the second housing member 4. Note that the end of the lumen 42 is tapered as a flare, so as to be suitable to disperse or converge the liquid which flows through the inner cavity 42.

A seal ring (a seal member) 43 having a structure similar to the previously described embodiment is disposed in the outer periphery of the second housing member 4. When the second housing member 4 has been inserted into the first housing member 3, the seal ring 43 is brought into close contact with the inner surface of the first housing member 3 so that the liquid-tightness of the housing 2, particularly, the aseptic characteristic is maintained.

When the second housing member 4 is moved with respect to the first housing member 3 in the axial direction, the seal ring 43 slides on the inner surface of the first housing member 3 while being in close contact with the inner surface 3.

An adjustment member 9 for adjusting the axial directional distance from the first housing member 3 to the second housing member 4 is attached to the housing 2. The adjustment member 9 comprises a base portion 91 having, in the central portion thereof, an opening 92, through which the second port is enabled to pass; and a cylindrical side wall 93 formed in the outer periphery of the base portion 91. The cylindrical side wall 93 has, on the inner surface thereof, a female thread 94 arranged to be engaged to the male thread 95.

The filter apparatus 1C has a filter member 5 and flow-passage maintaining members 6a and 6b formed similarly to the previously-mentioned embodiments.

The filter apparatus 1C has a porosity changing means which is composed of the adjustment member 9; and the male thread 95 formed in the outer periphery of the first housing member 3, the porosity changing means being structured to change the porosity of the filter member 5.

When the adjustment member 9 of the filter apparatus 1C having the above-mentioned structure is rotated in a predetermined direction with respect to the first housing member 3 in a state where the filter member 5 and the flow-passage maintaining members 6a and 6b are mounted in the housing 2 (that is, in a state where the filter apparatus 1C has been assembled) as shown in FIG. 8, the base portion 91 of the adjustment member 9 presses the second housing member 4. Thus, the second housing member 4 is moved to be deeply inserted into the first housing member 3. As a result, the filter member 5 is compressed, as shown in FIG. 9. When the adjustment member 9 is rotated with respect to the first housing member 3 in a direction opposite to the direction in the above-mentioned step, the restoring force of the filter member 5 causes the second housing member 4 to be moved in a direction in which the second housing member 4 is separated from the first housing member 3. Thus, the compressive force acting on the filter member is suspended.

As described above, if the amount of the relative rotation of the adjustment member 9 with respect to the first housing member 3, that is, the degree of screwing between the female thread 94 and the male thread 95 is adjusted, the insertion depth of the second housing member 4 into the first housing member 3 is adjusted and determined. Corresponding to the insertion depth above, the compressive force acting on the filter member 5, that is, the porosity (the pore size) of the filter member 5 can be adjusted.

Also the method of separating micro-tissues of an organism using the filter apparatus 1C is arranged similar to that of the filter apparatus 1A, except that the operation for changing porosity of filter member in the steps [1-A] and [4-A] is conducted by adjusting the rotational direction and the amount of the rotation of the adjustment member 9 with respect to the first housing member 3.

The foregoing cell separation method is also able to significantly improve the recovery ratio of the objective cells and the removal ratio of matters except the objective cells.

Figure 10:
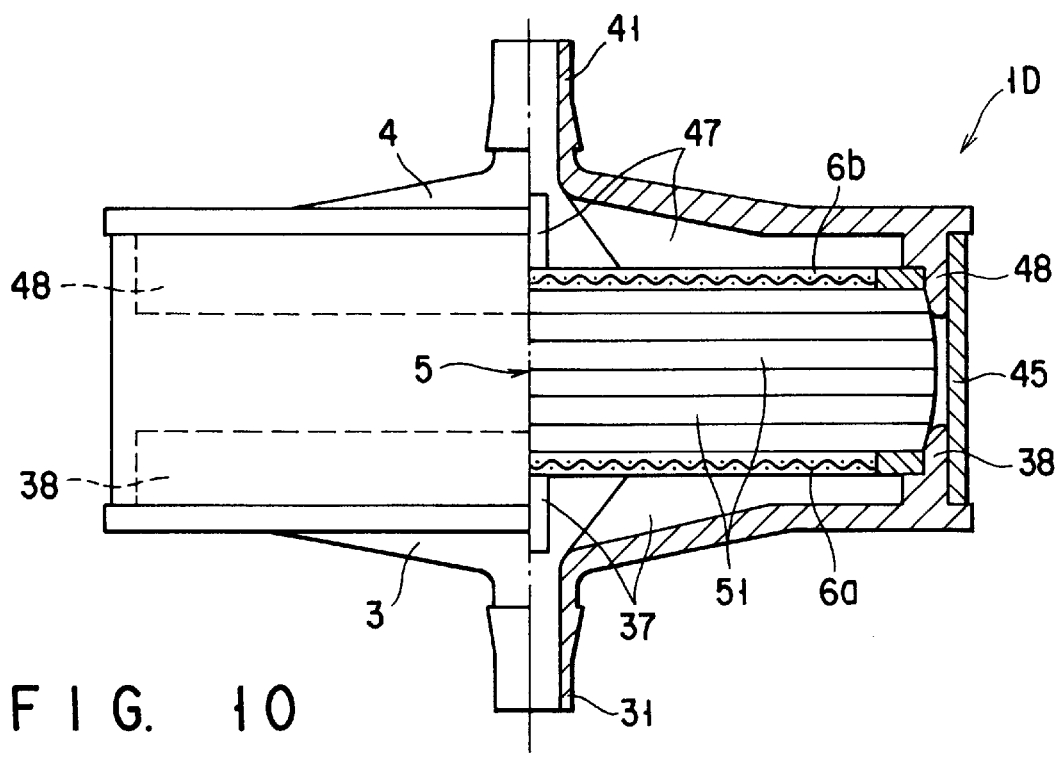
FIG. 10 is a partial cross sectional side view showing a fourth embodiment of the filter apparatus according to the present invention.
Figure 11:
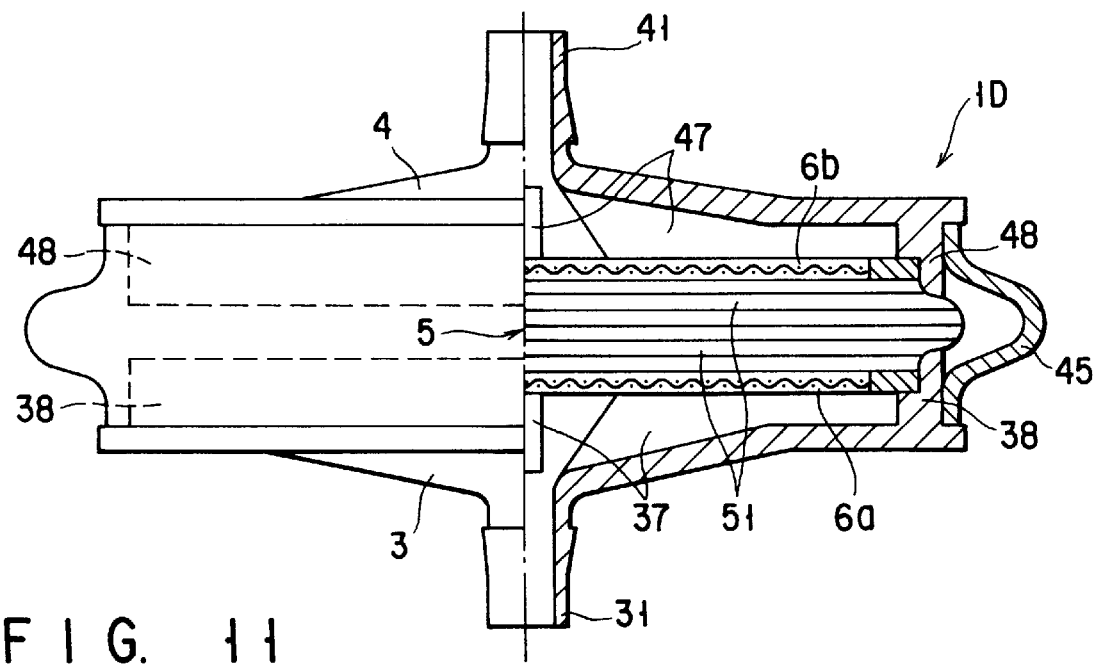
FIG. 11 is a partial a partial cross sectional side view showing the fourth embodiment of the present invention.

FIGS. 10 and 11 are partial cross sectional side views showing a fourth embodiment of the filter apparatus according to the present invention. A filter apparatus 1D shown in FIGS. 10 and 11 will now be described such that the difference from the filter apparatus 1A is mainly described and similar elements are omitted from description.

The filter apparatus 1D has a housing 2, a filter member 5 which is disposed in the housing 2 and has a structural similarity as that according to the previous embodiments, and flow-passage maintaining members 6a and 6b.

The housing 2 is formed by a first housing member 3 and a second housing member 4 having substantially symmetrical shapes.

Each of the first housing member 3 and the second housing member 4 has, in the central portion thereof, a first port (an inlet port of the liquid to be processed) 31 and a second port (an outlet port of a filtrate) 41 which are respectively communicated with the inside portion of the housing 2 and respectively project downward and upward.

The first housing member 3 and the second housing member 4 have, on the inside portion thereof, a plurality of plate-like ribs 37 and 47 for pressing the flow-passage maintaining members 6a and 6b for compressing the filter member 5. The plural ribs 37 and 47 are disposed in the radial direction from the central axis of the housing 2.

The filter member 5 and the flow-passage maintaining members 6a and 6b of the filter apparatus 1D have structures similar to the above-mentioned embodiments.

The first housing member 3 and the second housing member 4 have seal-member fixing portions 38 and 48 formed opposite to each other for securing the seal member 45.

The seal member 45 having a cylindrical shape is disposed in the outer periphery of the housing 2.

The seal member 45 is made of an elastic material, such as rubber or a thermoplastic elastomer, two axial directional ends of the seal member 45 being bonded or fused to the seal-member fixing portions 38 and 48 so as to be liquid-tightly secured to the housing 2.

When the filter member 5 is not compressed as shown in FIG. 10, the seal member 45 is formed into substantially the cylindrical shape. When the filter member 5 is compressed as shown in FIG. 11, the seal member 45 is deformed such that the central portion of the seal member 45 projects outwards.

As a result of the seal member 45 is provided as described above, the liquid-tightness of the housing 2, particularly the aseptic characteristic can be maintained regardless of whether or not the filter member 5 is compressed.

The shape of the seal member 45 is not limited to the illustrated shape. For example, a bellows shape may be employed. The seal member 45 may be secured to the inner side portions of the seal-member fixing portions 38 and 48.

The filter apparatus 1D having the structure described above is able to change or adjust the porosity (the pore size) of the filter member 5 by using the porosity changing means 7 described in the first and the second embodiments to shorten or elongate the direction from the first housing member 3 to the second housing member 4.

The method of separating micro-tissues of an organism having the filter apparatus 1D according to the present invention is also able to be performed similarly to the steps [1-A] to [5-A] described in reference to the first embodiment.

The cell separation method according to this embodiment is also able to significantly improve the recovery ratio of the objective cells and the removal ratio of matters other than the objective cells.

Figure 12:
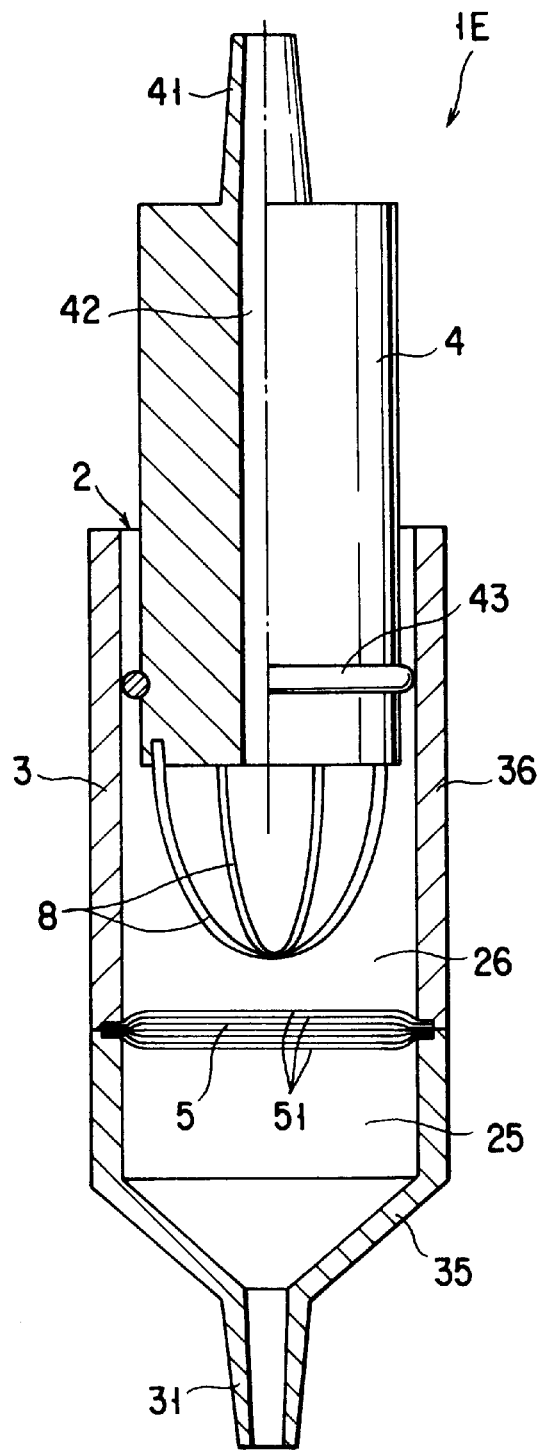
FIG. 12 is a cross sectional side view showing a fifth embodiment of the filter apparatus according to the present invention.
Figure 13:
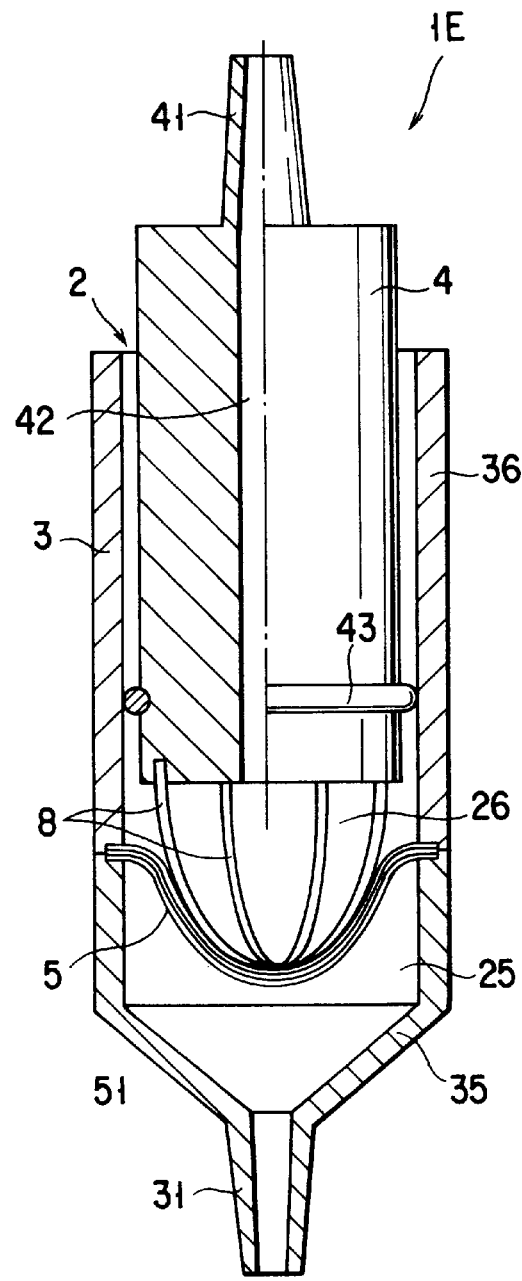
FIG. 13 is a cross sectional side view showing the fifth embodiment of the filter apparatus according to the present invention.

FIGS. 12 and 13 are cross sectional side views showing another embodiment of the filter apparatus according to the present invention. The filter apparatus 1E shown in FIGS. 12 and 13 will now be described such that similar elements as those of the filter apparatus 1A are omitted from illustration.

The filter apparatus 1E has a housing 2; and a filter member 5 disposed in the housing 2 and having a structure similar to that according to the above-mentioned embodiments.

The housing 2 is composed of a first housing member 3 having the proximal bottom end in which a first port 31 is formed; and a substantially cylindrical second housing member 4 inserted into the first housing member 3 and having a second port 41 at the distal top end thereof. The second port 41 is communicated with the inside portion of the housing 2 through an lumen 42 penetrating the central portion of the second housing member 4.

A seal ring 43 having a structure similar to that according to the previous embodiments is disposed on the outer periphery of the second housing member 4 so that the liquid-tightness of the housing 2, particularly, the aseptic characteristic is maintained.

The first housing member 3 is formed by bonding or fusing a proximal bottom member 35 having a first port 31 and a cylindrical distal member 36 to each other. The outer periphery of the filter member 5 is held and secured between the proximal bottom member 35 and the distal member 36. As a result, the inside portion of the housing 2 is, by the filter member 5, divided into a space 25 communicated with the first port 31 and the space 26 communicated with the second port 41. Note that the outer periphery of the filter member 5 may be bonded and secured to the first housing member 3 by an adhesive composition.

The filter member 5 is formed by porous polymer sheets similar to those according to the previously-described embodiments or a layer of the porous polymer sheets. Although the filter member 5 in this embodiment is formed by a laminating six layers of the porous polymer sheets so as to have the gradient of physical or chemical characteristics as described above, the filter member may be structured such that all or a portion of the porous polymer sheets 51 are the same. As an alternative to this, the filter member 5 may be formed by only one porous polymer sheets 51.

A bridge 8 for pressing and stretching the filter member 5 is secured to the proximal end of the second housing member 4. The bridge 8 is in the form such that a plurality of wires or plates are curved into, for example, parabolic or circular-arc shape which is convex toward the filter member 5, the bridge 8 having a predetermined rigidity capable of pressing the filter member 5.

In this embodiment shown in FIG. 12, the bridge 8 formed into a symmetrical shape with respect to the axis of the housing 2, is able to uniformly stretch the filter member 5. Therefore, variation or scattering of the second porosity (the second pore size) in the portions of the filter member 5 can be prevented.

The bridge 8 has another function serving as a spacer for preventing close contact between the proximal end surface of the second housing member 4 and the filter member 5. Thus, the bridge 8 also functions as the flow-passage maintaining member described in previous embodiments.

The filter apparatus 1E having the foregoing structure is operated such that the insertion depth of the second housing member 4 with respect to the first housing member 3 is manually adjusted to stretch the filter member 5 or to release relax the stretching of the filter member 5.

That is, as shown in FIG. 12, the insertion depth of the second housing member 4 with respect to the first housing member 3 is adjusted to a state in which the bridge 8 does not come in contact with the filter member 5 (or a state where the same is in lightly contact with the filter member 5). As a result, the filter member 5 is brought to a state where it is not applied with any tension or external force (or a state where the tension has been weakened). As a result, the porosity (the pore size) of the filter member is set to be the first porosity (the first pore size) suitable to capture the objective cells.

On the other hand, as shown in FIG. 13, the second housing member 4 is inserted deeply into the first housing member 3 so that the filter member 5 is pressed by the bridge 8. As a result, a tension acts on the filter member 5 so that the filter member 5 is stretched into a predetermined shape and the porosity (the pore diameter) of the filter member 5 is raised. Thus, the porosity (the pore diameter) is set to be the second porosity (the second pore size) suitable to detach the captured objective cells.

Although not illustrated in FIGS. 12 and 13, the filter apparatus 1E may also have a structure (not shown) such that a plurality of the seal rings 43 are disposed in the axial direction of the filter apparatus 1E. In addition, a porosity changing means including the thread projections 32 and the thread grooves 44 or the adjustment member 9 each of which has a shape similar to that of the previous embodiments may be provided in order to adjust the insertion depth of the second housing member 4 with respect to the first housing member 3 to set the desired porosity (the pore diameter).

An example of the method of separating micro-tissues of an organism using the filter apparatus 1E, which is in accordance with the present invention will now be described.

1-B

Initially, the insertion depth of the second housing member 4 with respect to the first housing member 3 is, as shown in FIG. 12, adjusted to a state where the bridge 8 does not come into contact with the filter member 5 (or a state where the bridge lightly comes into contact with the filter member 5). As a result, the pore size of the filter member 5 is set to be the first pore size capable of capturing the objective cells.

2-B

Then, cell suspension solution (solution to be processed) including the objective cells is supplied into the housing 2 through the first port 31 of the first housing member 3. The cell suspension solution is introduced into the space 25, and then allowed to pass through the filter member 5. At this time, the objective cells cannot pass through the pores of the filter member 5 set to the first pore size. Other components (unnecessary components) are allowed to pass through the pores, and then caused to sequentially flow the space 26 and the lumen 42 of the second housing member 4, followed by discharging the other components through the second port 41. Thus, the objective cells can be filtered and separated from the cell suspension solution.

3-B

After the objective cells have been filtered, washing solution is supplied through the first port 31, if necessary, to wash the inside portion of the housing 2, particularly, the filter member 5. As a result, unnecessary components adhered to the inner surface of the housing 2 and the filter member 5 are washed off so as to be discharged through the second port 41. In the washing process, the porosity (the pore size) of the filter member 5 is set similar to that of the previous embodiments.

4-B

Then, the second housing member 4 is, as shown in FIG. 13, slid into the deep portion of the first housing member 3 so as to cause the bridge 8 to press the filter member 5. As a result, the filter member 5 is stretched so that the pore size of the filter member 5 is set to the second pore size.

5-B

In the above-mentioned state, liquid for recovering the objective cells is supplied through the second port 41. The recovering liquid is introduced into the space 26 through the lumen 42 so as to be allowed to pass through the filter member 5. At this time, the objective cells captured by the filter member 5 are detached from the filter member 5 due to the flow of the recovering liquid. In particular, the enlargement of the pore size up to the second pore size causes the objective cells having been introduced into the pores to be removed from the pores, that is, detached and separated from the filter member 5. The objective cells separated from the filter member 5 are, with the flow of the solution, allowed to pass through the space 25, and then discharged through the first port 31 so as to be recovered.

As a result of the cell separation and recovery method described above, the recovery ratio of the objective cells and the removal ratio of matters other than the objective cells can significantly be enhanced, similarly to the case where the filter apparatus 1A is employed.

Incidentally, although each of the illustrated filter apparatuses 1A to 1E according to the present invention employs the filter member 5 comprising the laminate of plural porous polymer sheets each of which is different with respect to a particular physical or chemical characteristics so as to generate the gradient of the physical or chemical characteristic, the structure is not limited to this. For example, use may be made of a single integral porous sheet which has been formed so as to generate the gradient of the physical or chemical characteristics in the direction of the thickness of the sheet.

Examples of the present invention will now be described.

EXAMPLE 1

A filter apparatus of compressing-releasing type having the structure as shown in FIGS. 1 to 4 was manufactured.

The capacity of the housing was set to be in a range from 1.4 ml to 4.0 ml. A filter member was employed, which was a laminate (having a total thickness of 3.6 mm) formed by stacking six polyurethane porous sheets each having an effective diameter of 25 mm and a thickness of 0.6 mm.

A silicone rubber ring which has an inner diameter of 25 mm and a thickness of 1 mm as well as an outer diameter substantially the same as that of the porous sheet was provided with a polyamide mesh having a thickness of 0.6 mm inserted into the space inside of the ring. The silicone rubber ring with polyamide mesh was laminated and attached to each surface of the filter member.

As the seal ring, the one made of silicone rubber was used.

A porosity or pore size setting means (a compressing apparatus) was used as described previously, and measurement was made of the average pore diameter and the porosity in a state where no compressive force was applied to the filter member as well as the average pore diameter and a porosity in a state where the filter member was compressed to the total thickness of 1.4 mm. As a result, the average pore diameter was 6 µm and the porosity was 85% in the non-compressive state, while the average pore diameter was 3 µm and the porosity was 60% in the compressed state.

The average pore diameter was measured by a Palm Porometer (PMI Automated Capillary Flow Porometer manufactured by PMI). The porosity was obtained from the true specific gravity of the urethane and the bulk specific gravity of the filter member.

Experiment 1

The above-mentioned filter apparatus was used to perform an experiment for separating and recovering lymphocyte (the objective cells) from human whole blood.

First, the filter member was brought to the compressed state, and then 20 ml of human whole blood which has been made to be anticoagulant by adding citric acid was continuously supplied through a first port (at a supply speed of 2 ml/minute to 4 ml/minute) so as to filter and separate lymphocyte. Substantially no lymphocyte was detected in the blood component discharged through the second port. Thus, lymphocyte was perfectly captured by the filter member.

Then, 3 ml of phosphate buffer (hereinafter called as "PBS") was supplied (at a supply speed of 6 ml/minute) through the first port so that the inside portion of the housing was washed.

Then, the compressive force applied to the filter member was released so that the filter member was restored to the original thickness. In the restored state, 20 ml of PBS was supplied (at a supply speed of 120 ml/minute) through the second portion so that the lymphocyte discharged through the first port was recovered together with PBS.

The number of cells in the recovered solution was counted by a cell counter so that the recovery ratio of lymphocyte was obtained. Similarly, recovery ratio of granulocyte, monocyte, erythrocyte and thrombocyte, which were unnecessary components in the recovered solution were obtained. Results are shown in the following Table 1.

The survival ratio and the function of washed lymphocyte were not changed from that before the washing operation. Thus, no damage of lymphocyte was confirmed.

Comparative Example 1

Using an apparatus similar to that of in Example 1 was used, and Experiment was performed such that the sequential process from filtration of lymphocyte to recovery of the same was performed as similar to the foregoing example 1 except that the filter member was retained in the compressive state.

Similarly to the foregoing example 1, the recovery ratios of lymphocyte and unnecessary components were obtained. Results are shown in the following Table 1.

TABLE 1

|  | Recovery ratio of lymphocyte (%) | Recovery ratio of granulocyte (%) | Recovery ratio of monocyte (%) | Recovery ratio of erythrocyte (%) | Recovery ratio of thrombocyte (%) | Change of pore rate (times) |
| --- | --- | --- | --- | --- | --- | --- |
| Example 1 | 93 | 22 | 26 | 2 | 10 | 1.42 |
| Comparative example 1 | 55 | 29 | 44 | 7 | 10 | 1.0 |

As shown in Table 1, Example 1 was resulted in the recovery ratio of lymphocyte, which was the objective cells, being significantly improved as compared with Comparative Example 1. Since the recovery ratio of the unnecessary components was low, improvement of the removal ratio of the unnecessary components was also confirmed.

EXAMPLE 2

Similar Experiment 1 was performed by a filter apparatus similar to that of Example 1 except that the compression was performed such that the average pore diameter was 3 mm and the porosity was 55% in the compressive state of the filter member.

Comparative Example 2

By a specific density centrifugal method using Ficoll solution (density=1.077), lymphocyte was separated and recovered from human whole blood.

20 ml of Ficoll liquid was received in a 50 ml centrifugal sedimentation tube, and then 30 ml of human whole blood was gently superimposed as a layer. Then, a centrifugal operation was performed at 1750 rpm for 30 minutes so that the lymphocyte layer was fractionated and recovered.

Comparative Example 3

A erythrocyte sedimentation method using gelatin was employed to separate and recover lymphocyte from human whole blood.

Human whole blood diluted to ½ with PBS was added to 3 w/v% gelatin PBS solution, and then the solution was inverted and blended to confirm sedimentation of erythrocyte within 20 minutes. Then, supernatant was recovered.

Comparative Example 4

By an erythrocyte sedimentation method using methyl cellulose, lymphocyte was separated and recovered from human whole blood.

5 parts by volume of human whole blood were added to one part by volume of PBS solution of 1 w/v% methylcellulose, and then the solution was inverted and blended. Then, the solution was allowed to still stand for 30 minutes. After erythrocyte was settled down, the supernatant fluid was recovered.

In the Examples 2 and Comparative Examples 2 to 4, the recovery ratio of lymphocyte and removal ratio (=100−recovery ratio (%)) of each of unnecessary components were obtained similarly to the foregoing Example. Results are shown in the following Table 2.

TABLE 2

|  | Method | Recovery ratio of lymphocyte (%) | Removal ratio of granulocyte (%) |
| --- | --- | --- | --- |
| Example 2 | Compression-release method | 90.42 ± 5.58 | 71.63 ± 13.03 |
| Comparative example 2 | Ficoll method | 63.95 ± 17.14 | 92.50 ± 3.64 |
| Comparative example 3 | Gelatine method | 75.47 ± 13.87 | 19.12 ± 16.65 |
| Comparative example 4 | Methyl cellulose method | 64.20 ± 11.79 | 40.41 ± 17.70 |

|  | Removal ratio of monocyte (%) | Removal ratio of erythrocyte (%) | Removal ratio of thrombocyte (%) |
| --- | --- | --- | --- |
| Example 2 | 64.62 ± 7.70 | 95.80 ± 1.98 | 89.27 ± 5.08 |
| Comparative example 2 | 57.83 ± 34.14 | 99.97 ± 0.08 | 91.08 ± 4.69 |
| Comparative example 3 | 46.85 ± 14.58 | 96.15 ± 1.86 | 93.26 ± 3.89 |
| Comparative example 4 | 53.74 ± 20.17 | 96.84 ± 2.90 | 98.26 ± 1.61 |

Example 2 was confirmed that significant recovery ratios of lymphocyte of the objective cells were realized while maintaining high removal ratios of unnecessary components as compared with Comparative Examples 2 to 4 which were the methods other than the filtration method.

It was confirmed that Example 2 was able to process blood in the same quantity in a shorter time as compared with Comparative Examples 2 to 4. Therefore, the method according to Example 2 was suitable to quickly process a large quantity of blood.

EXAMPLE 3

A filter apparatus of compression-release type, which has the structure shown in FIGS. 5 to 7 was manufactured.

The capacity of the housing was made to be in a range from 1.4 ml to 4.0 ml.

A filter member was employed which was a layer (having a total thickness of 3.6 mm) of the following three types of polyurethane porous sheets respectively having (1) an effective diameter of 25 mm, a thickness of 0.6 mm, an average pore diameter of 9 $\mu$m and a porosity of 84%; (2) an effective diameter of 25 mm, a thickness of 0.6 mm, an average pore diameter of 6 $\mu$m and a porosity of 81%; and (3) an effective diameter of 25 mm, a thickness of 0.6 mm, an average pore diameter of 4 $\mu$m and a porosity of 84%. The laminating operation was performed such that two filter members of the each type (total six filter members) were sequentially stacked in such the manner that the average pore size is decreases from the portion adjacent to the first port. A silicone rubber ring (having an inner diameter or 25 mm and a thickness of 1 mm) and having an outer diameter which was substantially the same as that of the porous sheet was provided with a polyamide mesh (having a thickness of 0.6 mm) inserted into the inside space of the ring. The silicone ring provided with the polyamide mesh were overlaid and attached to the top and bottom surface of the filter member.

The two seal rings used in this Example were that made of silicone rubber.

The porosity setting means was used as described previously so that the filter member was set to a state where no compressive force was applied and a state where the filter member was compressed to the total thickness of 1.6 mm.

In the compressed state, The average pore diameters of the polyurethane porous sheets (1), (2) and (3) were 5 $\mu$m, 3 $\mu$m and 2 $\mu$m, respectively. The porosity of the polyurethane porous sheets (1), (2) and (3) were 64%, 57% and 64%, respectively. Incidentally, the average pore diameter was measured by an apparatus having a structure similar to the foregoing example.

The filter members described above were experimented similarly to Experiment 1 except for using the different sample (human whole blood) so that the recovery ratio of lymphocyte which were objective cells, and the recovery ratios of granulocyte, monocyte, erythrocyte and thrombocyte which were unnecessary components were obtained. Moreover, the time required for the supplying blood to pass through was measured. Results are shown in the following Table 3.

The survival ratio and the function of lymphocyte after the washing were not changed from those before the washing. Therefore, no damage of the lymphocyte was confirmed.

TABLE 3

|  |  | (Diameter of pore) | | | | | |
| --- | --- | --- | --- | --- | --- | --- | --- |
|  |  | Lymphocyte ($10^2/\mu l$) | Granulocyte ($10^2/\mu l$) | Monocyte ($10^2/\mu l$) | Erythrocyte ($10^4/\mu l$) | Thrombocyte ($10^4/\mu l$) | Fluid supplying period (minutes', seconds") |
| Example 3 | Amount before recovery | 13.9 | 24.9 | 2.2 | 438 | 15.0 | 7'48" |
|  | Amount after recovery | 13.0 | 10.6 | 0.6 | 8 | 2.4 |  |
|  | Recovery ratio | 93.5 | 42.6 | 27.3 | 1.8 | 16.0 |  |

EXAMPLE 4

An apparatus similar to that according to Example 3 was manufactured except that use was made of the filter member in which six polyurethane porous sheets of the same structure (1) have been stacked (a total thickness was 3.6 mm), and then similar Experiment 1 was performed.

Similarly to the foregoing examples, the recovery ratios of lymphocyte and unnecessary components and time required for the sample liquid to pass through were obtained. Results were shown in the following Table 4.

EXAMPLE 5

An apparatus similar to that according to Example 3 was manufactured except that use was made of the filter member in which six polyurethane porous sheets of the same structure (2) have been stacked (a total thickness was 3.6 mm), and then similar Experiment 1 was performed.

Similarly to the foregoing examples, the recovery ratios of lymphocyte and unnecessary components and time required for the solution to pass through were obtained. Results were shown in the following Table 4.

EXAMPLE 6

An apparatus similar to that according to Example 3 was manufactured except that use was made of the filter member in which six polyurethane porous sheets of the same structure (3) have been stacked (a total thickness was 3.6 mm), and then similar Experiment 1 was performed.

Similarly to the foregoing examples, the recovery ratios of lymphocyte and unnecessary components were obtained. Results were shown in the following Table 4.

Particularly, in Example 3, both high recovery ratio of the objective cells and a high removal ratio of unnecessary components were compatibly realized since use was made of the filter member having pores, the diameters of which has a suitable gradient.

EXAMPLE 7

A filter apparatus similar to that of Example 3 was manufactured except that use was made of a filter member which was formed by laminating six polyurethane porous sheets of two types having different zeta potentials, and each sheet having an effective diameter of 25 mm, a thickness of 0.6 mm, an average pore diameter of 6 $\mu$m and a porosity of 81%. Then, similar Experiment 1 was performed.

Lamination was performed such that four porous sheets each having a negative zeta potential (−4.6 mV) were laminated and then two porous sheet each having a positive zeta potential (+16.3 mV) were laminated starting from the portion adjacent to the first port. The total thickness of 3.6 mm was realized.

The average pore diameter of the compressed filter member was 3 $\mu$m and the porosity in the same state was 57%.

The zeta potential was measured by using a Streaming Potential Analizer (ZP-10B manufactured by Shimadzu).

Similarly to the foregoing examples, the recovery ratios of lymphocyte and unnecessary components and the solution passing time were obtained. Results are shown in the following Table 5.

EXAMPLE 8

An apparatus similar to that of Example 7 was manufactured except that use was made of a filter member which was a laminate of six porous sheets having the negative zeta potential mentioned in Example 7. A total thickness was 3.6 mm. Then, similar Experiment 1 was performed.

TABLE 4

|  | Lymphocyte ($10^2/\mu l$) | Granulocyte ($10^2/\mu l$) | Monocyte ($10^2/\mu l$) | Erythrocyte ($10^4/\mu l$) | Thrombocyte ($10^4/\mu l$) | Fluid supplying period (minutes', seconds") |
|---|---|---|---|---|---|---|
| Amount before recovery | 13.9 | 24.9 | 2.2 | 438 | 15.0 | — |
| Example 4 Amount | 11.1 | 11.0 | 0.8 | 9 | 1.1 | 5'48" |
| Example 5 after | 11.3 | 7.5 | 0.4 | 8 | 3.1 | 15'36" |
| Example 6 recovery | 7.5 | 7.2 | 0.3 | 8 | 3.5 | — |
| Example 4 Recovery | 80.0 | 44.2 | 36.4 | 2.1 | 7.3 | — |
| Example 5 ratio (%) | 81.3 | 30.1 | 18.2 | 1.8 | 20.7 | — |
| Example 6 | 54.0 | 28.9 | 13.6 | 1.8 | 23.3 | — |

As shown in Tables 3 and 4, Examples 3 and 6 resulted in high recovery ratios of lymphocyte which were objective cells. Examples 3 and 5 resulted in high passage speed and short recovery time.

Similarly to the foregoing examples, the recovery ratios of lymphocyte and unnecessary components and the solution passing time were obtained. Results are shown in the following Table 5.

TABLE 5

| | (Zeta potential) | | | | | |
|---|---|---|---|---|---|---|
|  | Lymphocyte ($10^2/\mu l$) | Granulocyte ($10^2/\mu l$) | Monocyte ($10^2/\mu l$) | Erythrocyte ($10^4/\mu l$) | Thrombocyte ($10^4/\mu l$) | Fluid supplying period (minutes', seconds") |
| Amount before recovery | 19.0 | 35.2 | 3.3 | 489 | 9.3 | — |
| Example 7 Amount | 16.9 | 9.9 | 0.9 | 6 | 1.5 | 9'22" |
| Example 8 after | 16.7 | 13.7 | 1.3 | 8 | 2.7 | 11'06" |

TABLE 5-continued (Zeta potential)

|  |  | Lympho-cyte ($10^2/\mu l$) | Granulo-cyte ($10^2/\mu l$) | Monocyte ($10^2/\mu l$) | Erythro-cyte ($10^4/\mu l$) | Thrombo-cyte ($10^4/\mu l$) | Fluid supplying period (minutes', seconds") |
|---|---|---|---|---|---|---|---|
|  | recovery |  |  |  |  |  |  |
| Example 7 | Recovery | 88.9 | 28.1 | 27.3 | 1.2 | 16.1 | — |
| Example 8 | ratio (%) | 87.9 | 38.9 | 39.4 | 1.6 | 29.0 | — |

As shown in Table 5, Examples 7 and 8 resulted high recovery ratios of lymphocyte which were objective cells and high removal ratios of unnecessary components.

Particularly in Example 7, Since the filter member having a gradient of zeta potential, the removal ratio of unnecessary components was improved while maintaining excellent recovery ratio of the objective cells. Therefore, the purity of the recovered objective cells could be improved. Moreover, the separation passing speed was raised.

EXAMPLE 9

A filter apparatus similar to that of Example 3 was manufactured except that use was made of a filter member which was formed by laminating six polyurethane porous sheets of three types having different hydrophilicities. Each of the six sheets had an effective diameter of 25 mm, a thickness of 0.6 mm, an average pore diameter of 6 $\mu$m and a porosity of 81%. Then, similar Experiment 1 was performed.

Lamination was performed such that two sheets of each type having hydrophilicity of 90 dyn/cm, 80 dyn/cm and 60 dyn/cm respectively, were sequentially stacked starting from the portion adjacent to the first port. The total thickness of 3.6 mm was realized.

The average pore diameter of the compressed filter member was 3 $\mu$m and the porosity in the same state was 57%.

The hydrophilicity was measured as the critical-wetting-surface tension (CWST) in accordance to a method disclosed in Unexamined Published Japanese Patent Application No. 3-27317.

Similarly to the foregoing examples, the recovery ratios of lymphocyte and unnecessary components and the solution passing time were obtained. Results are shown in the following Table 6.

EXAMPLE 10

A filter apparatus similar to that of Example 9 was manufactured except that use was made of a filter member which was a laminate of six porous sheets each having a hydrophilicity of 80 dyn/cm, the porous sheet being the same as that used in Example 9. Total thickness of the filter member was 3.6 mm. Then, similar experiment 1 was performed.

Similarly to the foregoing examples, the recovery ratios of lymphocyte and unnecessary components and the passing time were obtained. Results are shown in the following Table 6.

TABLE 6

(Hydrophilicity)

|  |  | Lympho-cyte ($10^2/\mu l$) | Granulo-cyte ($10^2/\mu l$) | Mono-cyte ($10^2/\mu l$) | Erythro-cyte ($10^4/\mu l$) | Thrombo-cyte ($10^4/\mu l$) | Fluid supplying period (minutes', seconds") |
|---|---|---|---|---|---|---|---|
|  | Amount before recovery | 17.2 | 26.1 | 2.4 | 466 | 16.7 | — |
| Example 9 | Amount after recovery | 16.6 | 9.9 | 0.8 | 7 | 2.4 | 10'18" |
| Example 10 |  | 15.8 | 12.2 | 0.9 | 10 | 1.6 | 9'00" |
| Example 9 | Recovery ratio (%) | 96.5 | 37.9 | 33.3 | 1.5 | 14.4 | — |
| Example 10 |  | 91.9 | 46.7 | 37.5 | 2.1 | 9.6 | — |

As shown in Table 6, Examples 9 and 10 resulted high recovery ratios of lymphocyte which were objective cells, and high removal ratio of unnecessary components.

Particularly, in Example 9, since the filter member has hydrophilicity gradient, the removal ratio of unnecessary components was improved while maintaining a high recovery ratio of the objective cells. Therefore, the purity of the recovered objective cells could be improved.

EXAMPLES 11 to 18

Eight types of filter apparatuses according to Examples 11 to 18 were manufactured under the same conditions as those employed in Examples 3 to 10 except for the structure of the apparatus being changed as shown in FIGS. 8 and 9 (capacity of the housing was 1.3 ml to 3.8 ml). Then, the filter apparatuses were subjected to similar Experiment 1.

As a result, Examples 11 to 18 resulted excellent recovery ratios of the objective cells and removal ratios of unnecessary components. The results of Examples 11 to 18 showed similar tendencies to those obtained from corresponding Examples 3 to 10.

EXAMPLES 19 to 26

Eight types of filter apparatuses according to Examples 19 to 26 were manufactured under the same conditions as those employed in Examples 3 to 10 except for the structure of the apparatus being changed as shown in FIGS. 10 and 11 (capacity of the housing was 1.8 ml to 4.8 ml; thickness of a seal member made of a styrene elastomer compound was 2 mm) and the porosity changing means shown in FIGS. 2 to 4. Then, the filter apparatuses were subjected to similar Experiment 1.

As a result, all of Examples 19 to 26 resulted excellent recovery ratios of the objective cells and removal ratios of unnecessary components. Examples 19 to 26 resulted similar tendencies to those obtained from corresponding Examples 3 to 10.

EXAMPLE 27

A filter apparatus of stretching-releasing type having a structure shown in FIGS. 12 to 13 was manufactured.

The capacity of the housing was determined to be in a range from 10.0 ml to 20.0 ml. As the filter member, a polyurethane porous sheet (single layer) having an effective diameter of 25 mm and a thickness of 1.8 mm was employed.

The insertion depth of the second housing member into the first housing member was adjusted, and the average pore diameter and the porosity were measured by a method similar to that employed in Example 1 in a state (in a non-stretched state) where no tension was applied to the filter member and a state where the filter member was stretched. In the non-stretched state, the average pore diameter was 4 μm and the porosity was 80%. In the stretched state, the average pore diameter was 6 μm and the porosity was 90%.

Experiment 2

The filter apparatus having the above mentioned structure was employed to perform an experiment to separate and recover lymphocyte which were the objective cells, from human whole blood which is different from the sample used in the foregoing experiment.

First, the filter member was brought to the non-stretched state, and then 20 ml of human whole blood made to be anticoagulant by adding citric acid was continuously supplied through a first port at a supply speed of 4 ml/minute, so as to filter and separate lymphocyte. The number of lymphocyte in the blood component discharged through the second port was about 2% of the number of lymphocyte in the blood before filtration. Thus, substantially the overall quantity of lymphocyte was captured by the filter member.

Then, 20 ml of PBS was supplied (supply speed was 6 ml/minute) through the first port so that the inside portion of the housing was washed.

Then, the filter member was brought to the stretched state, and then 20 ml of PBS was supplied in this state at supply speed of 60 ml/minute through the second portion. Then, lymphocyte discharged through the first portion was recovered together with PBS.

The number of cells in the recovered solution was counted by a cell counter so that the recovery ratios of lymphocyte as well as the recovery ratio of granulocyte, monocyte, erythrocyte and thrombocyte which were unnecessary components were obtained. Results are shown in the following Table 7.

The survival ratio and the function of washed lymphocyte were not changed from the state before the washing operation. Thus, no damage of lymphocyte was confirmed.

Comparative Example 5

An apparatus similar to that of Example 27 was used and Experiment 2 similar to the foregoing example was performed such that the sequential process from filtration of lymphocyte to recovery thereof was performed, except that the filter member was retained in the foregoing non-stretched state.

Similarly to the foregoing example, the recovery ratios of lymphocyte and unnecessary components were obtained. Results are shown in the following Table 7.

TABLE 7

|  | Recovery ratio of lymphocyte (%) | Recovery ratio of granulocyte (%) | Recovery ratio of monocyte (%) | Recovery ratio of erythrocyte (%) | Recovery ratio of thrombocyte (%) | Change of pore rate (times) |
| --- | --- | --- | --- | --- | --- | --- |
| Example 27 | 78 | 29 | 39 | 23 | 25 | 1.125 |
| Comparative example 5 | 61 | 44 | 52 | 43 | 48 | 1.0 |

As compared with Comparative Example 5, it was confirmed that Example 27 resulted in excellent recovery ratio of lymphocyte which was the objective cells, and the removal ratio of unnecessary components could be raised while retaining the high recovery ratio of the objective cells.

EXAMPLE 28

A filter apparatus of the stretch-release type having a structure shown in FIGS. 12 to 13 was manufactured.

The capacity of the housing was determined to fall within a range from 10.0 ml to 20.0 ml.

The filter member was a laminate of the three types of polyurethane porous sheets having the foregoing structures (1), (2) and (3), total thickness of the laminate being 3.6 mm. Lamination was performed such that two filter members of each type, i.e., totally six porous sheets, were sequentially stacked in the descending order of the average pore diameter starting from the portion adjacent to the first port.

In the state where no tension was applied to the filter member, i.e., non-stretched state and in a state where the filter member was stretched, the average pore diameter and the porosity were measured by using methods similar to those employed in Example 1. As a result, the average pore diameter (μm) and the porosity (%) of the porous sheets (1), (2) and (3) were as follows: (1) 12 μm, 91%; (2) 8 μm, 89%; and (3) 6 μm, 91%.

A seal ring made of silicone rubber was employed.

The filter member described above were experimented similarly to Experiment 2 except that the different sample of human whole blood was used, thereby obtaining the recovery ratio of lymphocyte which were objective cells, and the recovery ratios of granulocyte, monocyte, erythrocyte and thrombocyte which were unnecessary components. Moreover, the time required for supplying blood to pass through the filter member was measured. Results are shown in the following Table 8.

The survival ratio and the function of washed lymphocyte were not changed from those before washing. Therefore, no damage of the lymphocyte was confirmed.

time required for the sample liquid to pass through the filter apparatus were obtained. Results were shown in the following Table 9.

EXAMPLE 30

An apparatus similar to that of Example 28 was manufactured except for six polyurethane porous sheets all having the structure (2) were employed as the filter member, total thickness of the filter member being 3.6 mm. Then, similar experiment to Experiment 2 was performed.

Similarly to the foregoing examples, the recovery ratios of lymphocyte and unnecessary components, as well as the time required for the sample liquid to pass through the filter apparatus were obtained. Results were shown in the following Table 9.

EXAMPLE 31

An apparatus similar to that of Example 28 was manufactured except for six polyurethane porous sheets all having

TABLE 8

(Diameter of pore)

| | | Lymphocyte ($10^2/\mu l$) | Granulocyte ($10^2/\mu l$) | Monocyte ($10^2/\mu l$) | Erythrocyte ($10^4/\mu l$) | Thrombocyte ($10^4/\mu l$) | Fluid supplying period (minutes', seconds") |
|---|---|---|---|---|---|---|---|
| Example 28 | Amount before recovery | 16.7 | 22.1 | 1.1 | 380 | 11.3 | 9'24" |
| | Amount after recovery | 13.0 | 8.3 | 0.5 | 3 | 0.6 | |
| | Recovery ratio (%) | 77.8 | 37.6 | 45.5 | 0.8 | 5.3 | |

EXAMPLE 29

An apparatus similar to that of Example 28 was manufactured except for six polyurethane porous sheets all having the structure (1) were employed as the filter member, total thickness of the filter member being 3.6 mm. Then, similar experiment to Experiment 2 was performed.

Similarly to the foregoing examples, the recovery ratios of lymphocyte and unnecessary components, as well as the the structure (3) were employed as the filter member, total thickness of the filter member being 3.6 mm. Then, similar experiment to Experiment 2 was performed.

Similarly to the foregoing examples, the recovery ratios of lymphocyte and unnecessary components, as well as the time required for the sample liquid to pass through the filter apparatus were obtained. Results were shown in the following Table 9.

TABLE 9

| | | Lumphocyte ($10^2/\mu l$) | Granulocyte ($10^2/\mu l$) | Monocyte ($10^2/\mu l$) | Erythrocyte ($10^4/\mu l$) | Thrombocyte ($10^4/\mu l$) | Fluid supplying period (minutes", seconds") |
|---|---|---|---|---|---|---|---|
| Amount before recovery | | 16.7 | 22.1 | 1.1 | 380 | 11.3 | — |
| Example 29 | Amount | 4.1 | 6.0 | 0.5 | 2 | 0.5 | 4'22" |
| Example 30 | after | 11.5 | 9.7 | 0.4 | 3 | 1.0 | 8'32" |
| Example 31 | recovery | 10.0 | 10.9 | 0.4 | 4 | 2.1 | — |
| Example 29 | Recovery | 24.6 | 27.1 | 45.5 | 5.3 | 4.4 | — |
| Example 30 | ratio (%) | 68.9 | 43.9 | 36.4 | 7.9 | 8.8 | — |
| Example 31 | | 59.9 | 49.3 | 36.4 | 10.5 | 18.6 | — |

As shown in Tables 8 and 9, Examples 28 to 31 all resulted in high recovery ratios of lymphocyte which were objective cells. Examples 28 to 30 resulted in high passage speed and short recovery time.

Particularly in Example 28, Since the filter member having the gradient of the pore diameters was employed, both high recovery ratio of the objective cells and a high removal ratio of unnecessary components were compatibly realized.

EXAMPLE 32

A filter apparatus similar to that of Example 28 was manufactured except that use was made of a filter member which was formed by laminating six polyurethane porous sheets of two types having different zeta potentials. Each of the six sheets had an effective diameter of 25 mm, a thickness of 0.6 mm, an average pore diameter of 4 $\mu$m and a porosity of 84%. Then, similar Experiment 1 was performed.

Lamination was performed such that four porous sheets each having a negative zeta potential (−4.6 mV) were laminated and then two porous sheet each having a positive zeta potential (+16.3 mV) were laminated, starting from the portion adjacent to the first port. The total thickness of 3.6 mm was realized.

The average pore diameter of the stretched filter member was 6 mm and the porosity in the same state was 91%.

The zeta potential was measured by using a flow potential measuring apparatus previously described in the foregoing embodiment.

Similarly to the foregoing examples, the recovery ratios of lymphocyte and unnecessary components, as well as the time required for the sample liquid to pass through the filter apparatus were obtained. Results are shown in the following Table 10.

EXAMPLE 33

An apparatus similar to that of Example 32 was manufactured except that use was made of a filter member which was a laminate of six porous sheets each having the negative zeta potential, total thickness of the filter member being 3.6 mm. Then, similar Experiment 2 was performed.

Similarly to the foregoing examples, the recovery ratios of lymphocyte and unnecessary components, as well as the time required for the sample liquid to pass through the filter apparatus were obtained. Results are shown in the following Table 10.

As shown in Table 10, each of Examples 32 and 33 resulted high recovery ratios of lymphocyte which were objective cells and high removal ratios of unnecessary components. Moreover, high passage speed was realized.

Particularly in Example 32, since the filter member having the gradient of zeta potentials was used, the removal ratio of unnecessary components was improved while maintaining excellent recovery ratio of the objective cells. Therefore, the purity of the recovered objective cells could be improved.

EXAMPLE 34

A filter apparatus similar to that of Example 28 was manufactured except that use was made of a filter member which was formed by laminating six polyurethane porous sheets of three types having different hydrophilicities. Each of the six sheets had an effective diameter of 25 mm, a thickness of 0.6 mm, an average pore diameter of 4 $\mu$m and a porosity of 84%. Then, similar Experiment 2 was performed.

Lamination was performed such that two sheets of each type having hydrophilicity of 90 dyn/cm, 80 dyn/cm and 60 dyn/cm respectively, were sequentially stacked so that the hydrophilicity decreased starting from the portion adjacent to the first port. The total thickness of 3.6 mm was realized.

The average pore diameter of the stretched filter member was 6 $\mu$m and the porosity in the same state was 91%.

The hydrophilicity was measured by a method similar to that employed in the foregoing examples.

Similarly to the foregoing examples, the recovery ratios of lymphocyte and unnecessary components, as well as the time required for the sample liquid to pass through the filter apparatus were obtained. Results are shown in the following Table 11.

EXAMPLE 35

A filter apparatus similar to that of Example 34 was manufactured except that use was made of a filter member which was a laminate of six porous sheets each having a hydrophilicity of 80 dyn/cm, a total thickness of the filter member being 3.6 mm. Then, similar experiment 2 was performed.

Similarly to the foregoing examples, the recovery ratios of lymphocyte and unnecessary components, as well as the time required for the sample liquid to pass through the filter apparatus were obtained. Results are shown in the following Table 11.

TABLE 10

(Zeta Potential)

|  |  | Lymphocyte ($10^2/\mu l$) | Granulocyte ($10^2/\mu l$) | Monocyte ($10^2/\mu l$) | Erythrocyte ($10^2/\mu l$) | Thrombocyte ($10^4/\mu l$) | Fluid supplying period (minutes", seconds") |
|---|---|---|---|---|---|---|---|
| Amount before recovery | | 13.1 | 17.8 | 2.5 | 404 | 18.9 | — |
| Example 32 | Amount | 8.3 | 3.5 | 0.2 | 8 | 1.3 | 8'44" |
| Example 33 | after recovery | 8.1 | 7.8 | 0.6 | 7 | 2.9 | 8'22" |
| Example 32 | Recovery | 63.4 | 19.7 | 8.0 | 2.0 | 6.9 | — |
| Example 33 | ratio (%) | 61.8 | 43.8 | 24.0 | 1.7 | 15.3 | — |

TABLE 11

(Hydrophilicity)

|  |  | Lymphocyte ($10^2/\mu l$) | Granulocyte ($10^2/\mu l$) | Monocyte ($10^2/\mu l$) | Erythrocyte ($10^4/\mu l$) | Thrombocyte ($10^4/\mu l$) | Fluid supplying period (minutes", seconds") |
|---|---|---|---|---|---|---|---|
| Amount before recovery | | 13.1 | 17.8 | 2.5 | 404 | 18.9 | — |
| Example 34 | Amount | 9.2 | 3.0 | 0.3 | 6 | 1.1 | 7'30" |
| Example 35 | after recovery | 8.1 | 7.8 | 0.6 | 7 | 2.9 | 8'22" |
| Example 34 | Recovery | 70.2 | 16.9 | 12.0 | 1.5 | 5.8 | — |
| Example 35 | ratio (%) | 61.8 | 43.8 | 24.0 | 1.7 | 15.3 | — |

As shown in Table 11, Examples 34 and 35 resulted excellent recovery ratio of lymphocyte which were objective cells and high removal ratio of unnecessary components.

Particularly in Example 32, since the filter member having the gradient of hydrophilicity was used, the removal ratio of unnecessary components was improved while maintaining excellent recovery ratio of the objective cells. Therefore, the purity of the recovered objective cells could be improved.

The filter apparatus and the method of separating micro-tissues of an organism according to the present invention have been described referring to the illustrated embodiments. The present invention, however, is not limited to the foregoing embodiments.

First, the filter member is not limited to that which has been described in the foregoing embodiments. For example, the filter member may be a membrane filter or a filter made of an aggregate of fibers, such as woven or non woven fabric. The filter member is not limited to the elastically deformable member, but may be that which is plastically deformed when stretched and which maintains the deformed shape after release of the stretching force.

The means for providing the gradient of the physical or chemical characteristic of the filter member is not limited to that described in the foregoing embodiment, i.e., a combination of the porous sheets having the different average pore diameters, the combination of the porous sheets having different zeta potentials and the combination of the porous sheets having the different hydrophilicity. Any combinations of porous materials different in another physical or chemical characteristic may be employed. In addition, combination of two or more gradient of the foregoing characteristics may be employed.

The gradient of the physical or chemical characteristic may be realized in either of the state where the filter member is compressed or the state where the same is not compressed, or either of the state where the filter member is stretched or the state where the same is not stretched. For example, use may be made of a structure wherein the plural porous sheets of the filter member have different thicknesses (or degrees of elasticity), so that while the second porosity, i.e., porosity in the non-compressed state of the porous sheets are the same, the first porosity, i.e., the porosity in the compressed state of the porous sheets are made to be different from each other due to the difference in the thickness (or degrees of elasticity) of the porous sheets. As an alternative to this, a converse structure to the above structure may be employed.

The porosity of the filter member is not limited to the first and second porosities, but three or more porosities (pore size) may be provided. For example, a third porosity between the first porosity and the second porosity may be provided and the washing operation may be performed when the porosity is set to the third porosity.

In each of the foregoing embodiments, changing the porosity (the pore size) of the filter member is performed in order to realize a suitable porosity for both the separation (filtration) and recovery of the objective cells. The filter apparatus according to the present invention is not limited to the foregoing purpose. For example, a filter apparatus of the present invention may be employed for the purpose of separating different objective cells corresponding to each porosity by changing porosity (the pore size) of the filter member to be suitable to separate required objective cells. In other words, the filter apparatus according to the present invention may be used as a multi-purpose filter.

For example, the filter apparatus according to the present invention may be used such that the porosity is set to be the first porosity (the first pore size) to separate and recover lymphocyte, and set to the second porosity (the second pore size) to separate and recover other cells, such as erythrocyte or thrombocyte.

Micro-tissues of an organism required to be separated by the present invention, i.e., the objective micro-tissues of an organism are not limited to cells. For example, the micro-tissues may be cell nucleus, chromosomes, genes (DNA), structures on cell membranes, or organella.

As described above, according to the present invention, by using the filter member so as to change the porosity thereof, objective micro-tissues can be separated and recovered with a high yield without damage and denaturing, thereby maintaining the quality and the characteristic and so on thereof. Moreover, unnecessary components can be removed efficiently.

When the filter member has the gradient of physical or chemical characteristic, the foregoing effect can be improved.

When the filter member is formed by a laminate of a plurality of porous members, the physical or chemical characteristic can be set for each of the porous members. Therefore, the gradient of the characteristic can easily be provided for the filter member. Moreover, the degree of the gradient can easily be adjusted.

When the filter member, particularly, the elastic filter member is compressed or stretched to change the porosity, the porosity can easily be adjusted and set with excellent reproducibility while necessitating a simple structure.

When the ratio of the first porosity and the second porosity is set to be a desired value, or when the fluid-passage maintaining member is provided, when washing is performed, or when the porosity of the filter member during washing of the filter member is set to be a required level, the recovery ratio of the objective micro-tissues and the removal ratio of the unnecessary components can be further improved.

Furthermore, according to the present invention, the aseptic process, which is the advantage of the filtration method, can be performed, as well as a large-quantity process can be performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of separating cells from blood by using a filter member made of a porous material having a porosity which can be changed, the method comprising the steps of:

filtering the cells by using the filter member which is in such a state that the porosity of the filter member has been set to a first porosity capable of capturing the cells, said first porosity having a pore size less than 4.9 $\mu$m; and recovering the cells captured by the filter member, the recovery being performed in such a state that the porosity of the filter member has been set to a second porosity which is higher than the first porosity, the ratio of the second porosity to the first porosity being 1.05 to 3.0.

2. A method of separating cells according to claim 1, wherein the filter member comprises a laminate of a plurality of porous material.

3. A method of separating cells according to claim 1 wherein the filter member has a gradient of physical or a chemical characteristic in a direction along which the liquid flows.

4. A method of separating cells according to claim 3, wherein the gradient of physical or chemical characteristic comprises change of the diameter of pores of the porous material.

5. A method of separating cells according to claim 3, wherein the gradient of physical or chemical characteristic comprises change of the porosity of the porous material.

6. A method of separating cells according to claim 3, wherein the gradient of physical or chemical characteristic comprises change of the hydrophilicity of the porous member.

7. A method of separating cells according to claim 3, wherein the gradient of physical or chemical characteristic comprises change of the zeta potential of the porous material.

8. A method of separating cells according to claim 1, wherein the filter member has such a structure that rise and lowering of the porosity correspond to enlargement and reduction of the diameter of the pores, respectively.

9. A method of separating cells according to claim 1, including washing the filter member by supplying a washing liquid, said washing of the filter member being performed with the porosity of the filter member being higher than the first porosity and lower than the second porosity.

10. A method of separating cells from blood by using a filter apparatus which comprises a housing having first and second ports and accommodates a filter member made of porous material having a variable porosity, the method comprising the steps of:

supplying liquid to be treated containing the cells through the first port to the filter member and separating the cells by passing the liquid through the filter member in such a state that the porosity of the filter member has been set to a first porosity capable of capturing the cells, said first porosity having a pore size less than 4.9 $\mu$m; and supplying recovering liquid through the second port to the filter member in such a state that the porosity of the filter member has been set to a second porosity which is higher than the first porosity, thereby recovering the cells captured by the filter member, the ratio of the second porosity to the fist porosity being 1.05 to 3.0.

11. A method of separating cells according to claim 10, further comprising a fluid-passage maintaining member for maintaining a flowing passage of liquid which is introduced through the first port and/or the second port to the filter member.

12. A method of separating cells according to claim 10, including washing the filter member by supplying a washing liquid, said washing of the filter member being performed with the porosity of the filter member being higher than the first porosity and lower than the second porosity.

13. A method of separating cells from blood by using a filter apparatus which comprises a housing having first and second ports and accommodates a filter member made of porous material having a variable porosity, the method comprising the steps of:

supplying liquid to be treated containing the cells through the first port to the filter member and separating the cells by passing the liquid through the filter member in such a state that the porosity of the filter member has been set to a first porosity capable of capturing the cells, said first porosity having a pore size less than 4.9 $\mu$m;

supplying washing liquid through the first port, thereby washing the filter member; and supplying recovering liquid through the second port to the filter member in such a state that the porosity of the filter member has been set to a second porosity which is higher than the first porosity, thereby recovering the cells captured by the filter member, the ratio of the second porosity to the first porosity being 1.05 to 3.0.

14. A method of separating cells according to claim 13, wherein said washing step of the filter member is performed in such a state that the porosity of the filter member has been set to a level which is higher than the first porosity and lower than the second porosity.

15. A method of separating cells according to claim 13, wherein said washing step of the filter member is performed in such a state that the first porosity of the filter member is retained.

* * * * *